United States Patent
Harmon et al.

(10) Patent No.: US 11,564,919 B1
(45) Date of Patent: Jan. 31, 2023

(54) SMALL MOLECULE INHIBITORS FOR TREATMENT OF ALPHA VIRUSES

(71) Applicant: National Technology & Engineering Solutions of Sandia, LLC, Albuquerque, NM (US)

(72) Inventors: Brooke Nicole Harmon, Livermore, CA (US); Oscar Negrete, Livermore, CA (US); Joseph S. Schoeniger, Oakland, CA (US); Edwin A. Saada, Dublin, CA (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 107 days.

(21) Appl. No.: 17/189,596

(22) Filed: Mar. 2, 2021

(51) Int. Cl.
| | |
|---|---|
| *A61K 31/496* | (2006.01) |
| *A61P 31/14* | (2006.01) |
| *A61K 31/53* | (2006.01) |
| *A61K 31/428* | (2006.01) |
| *A61K 31/426* | (2006.01) |
| *A61K 9/00* | (2006.01) |

(52) U.S. Cl.
CPC .......... *A61K 31/496* (2013.01); *A61K 9/0029* (2013.01); *A61K 9/0053* (2013.01); *A61K 31/426* (2013.01); *A61K 31/428* (2013.01); *A61K 31/53* (2013.01); *A61P 31/14* (2018.01)

(58) Field of Classification Search
None
See application file for complete search history.

(56) References Cited

PUBLICATIONS

CDC, "What is Rift Valley Fever?", Centers for Disease Control and Prevention, last reviewed date Feb. 25, 2020, downloaded from www.cdc.gov/vhf/rvf/about.html on Aug. 9, 2022, 1 page (Year: 2020).*
Gladych et al., "Antiviral Agents. 5H-as-Triazino[5,6-b]indoles", Journal of Medicinal Chemistry, vol. 13(3), pp. 277-281, 1972. (Year: 1972).*
Bettadapura, et al., "Approaches to the Treatment of Disease Induced by Chikungunya Virus", In Indian J Med Res, vol. 138, Nov. 2013, pp. 762-765.
Bhakat, et al., "A Perspective on Targeting Non-Structural Proteins to Combat Neglected Tropical Diseases: Dengue, West Nile and Chikungunya Viruses", In European Journal of Medicinal Chemistry, vol. 87, 2014, pp. 677-702.
Damoiseaux, Robert, "UCLA's Molecular Screening Shared Resource: Enhancing Small Molecule Discovery With Functional Genomics and New Technology", In Combinatorial Chemistry & High Throughput Screening, vol. 17, 2014, pp. 356-368.
Gould, et al., Understanding the Alphaviruses: Recent Research on Important Emerging Pathogens and Progress Towards Their Control, In Antiviral Research, vol. 87, 2010, pp. 111-124.
Harmon, et al., "Identification of Broad Spectrum Inhibitors of Alphaviruses Using High-Throughput Screening", Sandia National Laboratories, Retrieved At: <<https://www.osti.gov/biblio/1484568-identification-broad-spectrum-inhibitors-alphaviruses-using-high-throughput-screening>>, 1 page.
Khan, et al., "Discovery of Small Molecule Inhibitors of Chikungunya Virus Proteins (nsP2 and E1) Using in Silico Approaches", In Journal of Biomolecular Structure and Dynamics, Taylor & Francis, Mar. 5, 2020, 15 pages.
Molport, "(2E)-3-(2H-1,3-benzodioxol-5-yl)-1-(4-{[4-(furan-2-yl)-1,3-thiazol-2-yl]methyl}piperazin-1-yl)prop-2-en-1-one", 2 pages.
Nguyen, et al., "Identification of Chikungunya Virus nsP2 Protease Inhibitors Using Structure-Base Approaches", In Journal of Molecular Graphics and Modelling, vol. 57, 2015, pp. 1-8.
Rashad, et al., "Chikungunya Virus: Emerging Targets and New Opportunities for Medicinal Chemistry", In Journal of Medicinal Chemistry, vol. 57, 2014, pp. 1147-1166.
Saada, et al., "Identification of Small-Molecule Inhibitors of Chikungunya Virus Using High-Throughput Screening", Sandia National Laboratories, Retrieved At: <<https://www.osti.gov/biblio/1365338>>, 1 page, (2016).
Schroeder, et al., "Developement of (E)-2-((1,4-Dimethylpiperazin-2-ylidene)amino)-5-nitro-N-phenylbenzamide, ML336: Novel 2-Amidinophenylbenzamides as Potent Inhibitors of Venezuelan Equine Encephalitis Virus", In Journal of Medicinal Chemistry, vol. 57, 2014, pp. 8608-8621.

* cited by examiner

*Primary Examiner* — Savitha M Rao
*Assistant Examiner* — Gregg Polansky
(74) *Attorney, Agent, or Firm* — Eschweiler & Potashnik, LLC; Madelynne J. Farber; Samantha Updegraff

(57) ABSTRACT

An in vitro assay was designed to measure the activity of the alphavirus non-structural protein 2 (nsP2), which is the viral protease and is required for viral replication. By taking advantage of fluorescence-resonance energy transfer between two proteins, a protease cleavage assay was generated. This was utilized for high-throughput screening of 40,000 small molecules. Inhibitors were validated using cell-based assays to measure alphavirus infection and cytotoxicity. Certain compounds were then characterized for anti-viral efficacy in various cell lines in numerous assays. Compounds were tested against Chikungunya virus, Venezuelan Equine Encephalitis virus, Rift Valley Fever virus, and Zika virus. Three compounds (compounds I, II, and III) showed pan-alphavirus anti-viral efficacy at concentrations that did not result in cell toxicity. An additional compound, structure IV, showed broad spectrum inhibition of all viruses tested. Pharmaceutical preparations and methods of treatment including these compounds are provided herein.

20 Claims, 11 Drawing Sheets
Specification includes a Sequence Listing.

Fig. 14

SMALL MOLECULE INHIBITORS FOR TREATMENT OF ALPHA VIRUSES

STATEMENT OF GOVERNMENT INTEREST

This invention was made with Government support under Contract No. DE-NA0003525 awarded by the United States Department of Energy/National Nuclear Security Administration. The Government has certain rights in the invention.

SEQUENCE LISTING

The instant application contains a Sequence Listing which has been submitted electronically in ASCII format and is hereby incorporated by reference in its entirety. Said ASCII copy, created on Jul. 16, 2021, is named SD14540_0_S148941_SL.txt and is 885 bytes in size.

FIELD

This disclosure relates to pharmaceutical preparations for treatment of alphaviruses and methods for treatment of alphaviruses.

BACKGROUND

Arthropod-borne viruses (arboviruses) are distributed worldwide and are important causes of human disease resulting in considerable human morbidity and mortality. Historically arboviral disease outbreaks occurred in tropical regions such as Africa, South America, and Asian countries, but in the past few decades, arboviral diseases have expanded into new regions in the world. West Nile virus underwent a dramatic geographic expansion into the Americas in 1999 resulting in the largest epidemic of arboviral encephalitis ever documented in the United States. Today, CHIKV has undergone a similar radical geographic emergence into the Americas. Traditionally, CHIKV epidemics have shown cyclical trends, with inter-epidemic periods ranging from 4 to 30 years. Since 2004, CHIKV has expanded its geographical range, causing sustained epidemics of unprecedented magnitude in Asia and Africa. In December 2013, the first autochthonous CHIKV cases were confirmed on the Caribbean island of St. Martin. Since then, CHIKV has continued to spread to neighboring countries, and it is probable that in the near future CHIKV will spread and remain endemic in the United States. As of 2016, there have been over 1.7 million suspected CHIKV infections in the Americas. In the United States, it is classified as a category C biodefense priority pathogen due to the ability to engineer this pathogen for mass dissemination causing high morbidity and mortality rates with nearly worldwide distribution. At present, there are no licensed vaccines or treatment options to combat CHIKV infection, and research in the development of therapeutics has been limited. Thus, there is a pressing need to identify and develop new therapeutic avenues.

Chikungunya virus (CHIKV) is a re-emerging alphavirus, that causes acute illness characterized by rapidly onset fever and severe arthralgia, and in many cases develops into a debilitating, chronic arthritis. There are no approved vaccines or treatment options available to combat CHIKV infection. The alphavirus nonstructural protein 2 (nsP2) is an attractive anti-viral target, since it participates in proteolytic processing of the nonstructural polyprotein into functional proteins, and is required for viral replication.

If identified, small molecules have the benefit of being cell penetrating, more suitable for oral delivery, and easier to manufacture than protein or other large molecule treatments.

SUMMARY

Alphaviruses are a serious biomedical concern. To find anti-viral inhibitors, an in vitro assay was designed to measure the activity of the alphavirus non-structural protein 2 (nsP2), which is the viral protease and is required for viral replication. By taking advantage of fluorescence-resonance energy transfer (FRET) between two proteins, a protease cleavage assay was generated. This was utilized for high-throughput screening of 40,000 small molecules. Inhibitors were validated using cell-based assays to measure alphavirus infection and cytotoxicity. Certain compounds were then characterized for anti-viral efficacy in various cell lines in numerous assays (viral reduction, infection by flow cytometry, viral titer reduction). Compounds were tested against Chikungunya virus (CHIKV) strain 181/25, CHIKV 181/25 GFP reporter strain, and Venezuelan Equine Encephalitis virus (VEEV), strain TC-83, Rift Valley Fever Virus (RVFV) strain MP12, and Zika virus (ZIKV). Three compounds, shown in structures I, II, and III below, showed pan-alphavirus anti-viral efficacy at concentrations that did not result in cell toxicity. An additional compound, structure IV, showed broad spectrum inhibition of all viruses tested including CHIKV, VEEV, RVFV, and ZIKV, without causing in vitro cell toxicity.

In an embodiment, a pharmaceutical composition comprises a compound selected from the group consisting of compounds I-IV:

pharmaceutically acceptable salts thereof, or combinations of any of these; and a pharmaceutically acceptable excipient.

In an embodiment, a method of treatment for an alphavirus infection comprises administering to a patient in need thereof, a therapeutically effective amount of a compound selected from the group consisting of compounds I-IV pharmaceutically acceptable salts thereof, or combinations of any of these; and a pharmaceutically acceptable excipient.

In an embodiment, a method of treatment for a Zika virus infection includes administering to a patient in need thereof a therapeutically effective amount of a compound selected from the group consisting of compound IV pharmaceutically acceptable salts thereof, or combinations of any of these; and a pharmaceutically acceptable excipient.

As used herein, the term "about" means +/−10% of any recited value. As used herein, this term modifies any recited value, range of values, or endpoints of one or more ranges.

The term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form. Additionally, as used herein, the term "exemplary" is intended to mean serving as an illustration or example of something and is not intended to indicate a preference.

By an "effective amount" or a "sufficient amount" of an agent (e.g., a molecule described herein), as used herein, is that amount sufficient to effect beneficial or desired results, such as clinical results, and, as such, an "effective amount" depends upon the context in which it is being applied.

By "subject" or "patient" is meant a human or non-human animal (e.g., a mammal).

By "treating" a disease, disorder, or condition in a subject is meant reducing at least one symptom of the disease, disorder, or condition by administrating a therapeutic agent to the subject. By "treating prophylactically" a disease, disorder, or condition in a subject is meant reducing the frequency of occurrence of or reducing the severity of a disease, disorder or condition by administering a therapeutic agent to the subject prior to the onset of disease symptoms. Beneficial or desired results can include, but are not limited to, alleviation or amelioration of one or more symptoms or conditions; diminishment of extent of disease, disorder, or condition; stabilized (i.e., not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable.

By "salt" is meant an ionic form of a compound or structure (e.g., any formulas, compounds, or compositions described herein), which includes a cation or anion compound to form an electrically neutral compound or structure. For example, non-toxic salts are described in Berge S M et al., "Pharmaceutical salts," *J. Pharm. Sci.* 1977 January; 66(1):1-19; and in "Handbook of Pharmaceutical Salts: Properties, Selection, and Use," Wiley-VCH, April 2011 (2nd rev. ed., eds. P. H. Stahl and C. G. Wermuth). The salts can be prepared in situ during the final isolation and purification of the compounds of the disclosed technology or separately by reacting the free base group with a suitable organic acid (thereby producing an anionic salt) or by reacting the acid group with a suitable metal or organic salt (thereby producing a cationic salt). Representative anionic salts include acetate, adipate, alginate, ascorbate, aspartate, benzenesulfonate, benzoate, bicarbonate, bisulfate, bitartrate, borate, bromide, butyrate, camphorate, camphorsulfonate, chloride, citrate, cyclopentanepropionate, digluconate, dihydrochloride, diphosphate, dodecylsulfate, edetate, ethanesulfonate, fumarate, glucoheptonate, glucomate, glutamate, glycerophosphate, hemisulfate, heptonate, hexanoate, hydrobromide, hydrochloride, hydroiodide, hydroxyethanesulfonate, hydroxynaphthoate, iodide, lactate, lactobionate, laurate, lauryl sulfate, malate, maleate, malonate, mandelate, mesylate, methanesulfonate, methylbromide, methylnitrate, methylsulfate, mucate, 2-naphthalenesulfonate, nicotinate, nitrate, oleate, oxalate, palmitate, pamoate, pectinate, persulfate, 3-phenylpropionate, phosphate, picrate, pivalate, polygalacturonate, propionate, salicylate, stearate, subacetate, succinate, sulfate, tannate, tartrate, theophyllinate, thiocyanate, triethiodide, toluenesulfonate, undecanoate, and valerate salts. Representative cationic salts include metal salts, such as alkali or alkaline earth salts, e.g., barium, calcium (e.g., calcium edetate), lithium, magnesium, potassium, and sodium; other metal salts, such as aluminum, bismuth, iron, and zinc; as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and pyridinium. Other cationic salts include organic salts, such as chloroprocaine, choline, dibenzylethylenediamine, diethanolamine, ethylenediamine, methylglucamine, and procaine. Exemplary salts include pharmaceutically acceptable salts.

By "pharmaceutically acceptable salt" is meant a salt that is, within the scope of sound medical judgment, suitable for use in contact with the tissues of humans and animals without, for example, undue toxicity, irritation, or allergic response, and are commensurate with a reasonable benefit/risk ratio.

By "pharmaceutically acceptable excipient" is meant any ingredient other than a compound or structure (e.g., any formulas, compounds, or compositions described herein) and having the properties of being nontoxic and non-inflammatory in a subject. Exemplary, non-limiting excipients include adjuvants, antiadherents, antioxidants, binders, carriers, coatings, compression aids, diluents, disintegrants, dispersing agents, dyes (colors), emollients, emulsifiers, fillers (diluents), film formers or coatings, flavors, fragrances, glidants (flow enhancers), isotonic carriers, lubricants, preservatives, printing inks, solvents, sorbents, stabilizers, suspending or dispersing agents, surfactants, sweeteners, waters of hydration, or wetting agents. Any of the excipients can be selected from those approved, for example, by the United States Food and Drug Administration or other governmental agency as being acceptable for use in humans or domestic animals. Exemplary excipients include, but are not limited to alcohol, butylated hydroxytoluene (BHT), calcium carbonate, calcium phosphate (dibasic), calcium stearate, croscarmellose, cross-linked polyvinyl pyrrolidone, citric acid, crospovidone, cysteine, ethylcellulose, gelatin, glycerol, hydroxypropyl cellulose, hydroxypropyl methylcellulose, lactated Ringer's solution, lactose, magnesium stearate, maltitol, maltose, mannitol, methionine, methylcellulose, methyl paraben, microcrystalline cellulose, polyethylene glycol, polyol, polyvinyl pyrrolidone, povidone, pregelatinized starch, propyl paraben, retinyl palmitate, Ringer's solution, shellac, silicon dioxide, sodium carboxymethyl cellulose, sodium chloride injection, sodium citrate, sodium starch glycolate, sorbitol, starch (corn), stearic acid, stearic acid, sucrose, talc, titanium dioxide, vegetable oil, vitamin A, vitamin E, vitamin C, water, and xylitol.

By "attaching," "attachment," or related word forms is meant any covalent or non-covalent bonding interaction between two components. Non-covalent bonding interactions include, without limitation, hydrogen bonding, ionic interactions, halogen bonding, electrostatic interactions, π bond interactions, hydrophobic interactions, inclusion complexes, clathration, van der Waals interactions, and combinations thereof.

BRIEF DESCRIPTION OF THE DRAWINGS

FIG. 14 is a series of bar graphs showing viral titers of parental CHIKV 181/25, VEEV TC-83, and RVFV MP12 measured in the presence of the compounds of interest.

DETAILED DESCRIPTION

Disclosed herein are small molecules that provide antiviral activity against alphaviruses. To identify effective inhibitors of CHIKV and other alphaviruses, a novel FRET-based assay was developed to monitor substrate cleavage by nsP2pro and optimized the assay to screen 40,000 compounds. Following initial validation, 101 compounds were chosen for secondary validation in cells to measure cytotoxicity and efficacy against CHIKV infection, which identified four promising compounds. The screening system provided a rapid and high-throughput way to find specific and broad spectrum therapeutic compounds. Four chemical compounds (small molecules) were identified through this method that had surprising antiviral effectiveness against alphaviruses.

Figure 2:
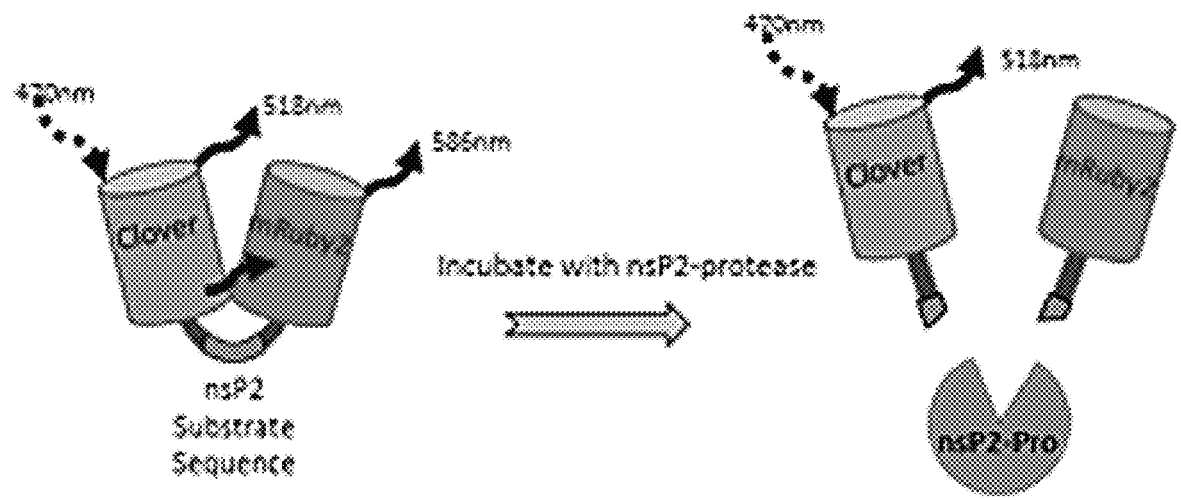
FIG. 2 is a graphic showing a vitro cell-free assay utilizing recombinant nsP2pro in conjunction with a FRET-enabled substrate.
Figure 3:
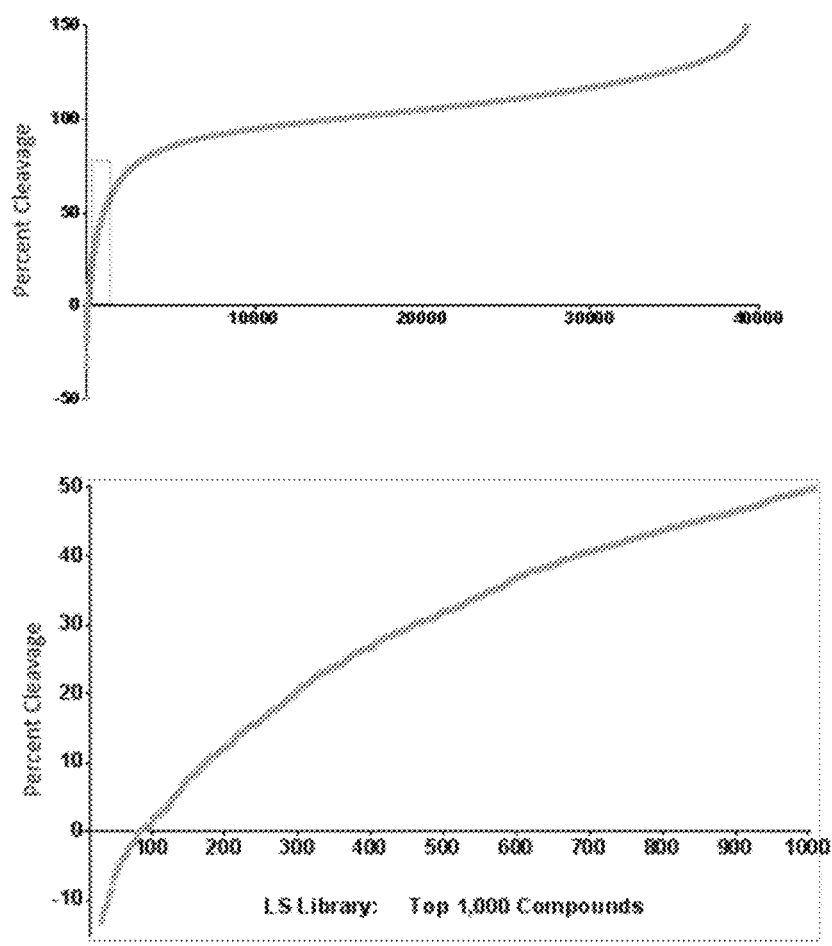
FIG. 3 are graphs showing the initial 4000 and the down-sampled top 1000 compounds, and their percent cleavage per FRET analysis.

The compounds found to be surprisingly effective as an antiviral; are shown in structures: I, II, III, and IV:

Compound I (internal designation as shown in figures. 2G3) has an IUPAC name of (2E)-3-(2H-1,3-benzodioxol-5-yl)-1-(4-{[4-(furan-2-yl)-1,3-thiazol-2-yl]methyl}piperazin-1-yl)prop-2-en-1-one. It corresponds to formula $C_{22}H_{21}N_3O_4S$, CAS 1105223-67-3, CID 30860541 and Molport ID 009-733-377. It has a molecular weight of 423.49 Da.

Compound II (internal designation as shown in figures: D10) has an IUPAC name of 2-hydroxy-4-[(5Z)-5-[(4-hydroxy-3-methoxyphenyl)methylidene]-4-oxo-2-sulfanylidene-1,3-thiazolidin-3-yl]benzoic acid. It corresponds to formula $C_{18}H_{13}NO_6S_2$, CID 620659, Molport ID 000-508-931, and Life Chemicals No. F1950-0060. It has a molecular weight of 403.43 Da.

Compound III (internal designation as shown in figures: A3) has an IUPAC name of 5H-[1,2,4]Triazino[5,6-b]indole-3-thiol. It corresponds to formula $C_9H_6N_4S$, CID 135403808 and Life Chemicals No. F0227-0536. It has a molecular weight of 202.24 Da.

Compound IV (internal designation as shown in figures: G8) has an IUPAC name of 3-methyl-2H,b3H-naphtho[2,1-d][1,3]thiazol-2-imine. It corresponds to formula $C_{12}H_{10}N_2S$, CAS 55065-85-5, and Molport ID 003-065-940, and Life Chemicals No. F1386-0371. It has a molecular weight of 214.29 Da.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Unless otherwise stated, all tautomeric forms of the structures disclosed herein are meant to be included by these structures. The structures also include zwitterionic forms of the compounds.

In an embodiment, more than one of these compounds can be used together. In addition, pharmaceutically acceptable salts of any of compounds I-IV may also be used. For example, S. M. Berge, et al. describe pharmaceutically acceptable salts in detail in, Pharmaceutical Sciences, 1977, 66, 1-19, incorporated herein by reference. Pharmaceutically acceptable salts of the compounds disclosed herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N+(C_{1-4}$ alkyl$)_4$ salts. Salts may also include quaternization of any basic nitrogen-containing groups of the compounds disclosed herein. In an embodiment, water or oil-soluble or dispersable products may be obtained by such quaternization. Example alkali or alkaline earth metal salts include sodium, lithium, potassium, calcium, and magnesium. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

In an embodiment, combinations of the any of the compounds and pharmaceutically acceptable salts thereof mentioned above may be used. Compounds that are additively synergistic in effectiveness can be administered at lower dosages, which may enhance suitability for therapeutic application and reduce off-target effects in vivo.

The compounds were found to be effective against alphaviruses. Alphaviruses are a genus of RNA viruses. Alphaviruses are small, spherical, enveloped, positive-sense single-stranded RNA viruses responsible for several human and animal diseases in various parts of the world. Alphaviruses are zoonotic pathogens that are maintained primarily in rodents, primates, and birds by mosquito vectors. Humans typically contract alphaviruses when they are bitten by infected mosquitoes, or when alphaviruses emerge to cause epizootics and epidemics.

Alphaviruses may be sub-classified as New or Old World alphaviruses. New World alphaviruses are distributed across the Americas, cause debilitating, acute and sometimes fatal encephalitis and include: Eastern equine encephalitis virus (EEEV), Western equine encephalitis virus (WEEV) and Venezuelan equine encephalitis virus (VEEV).

Old World alphaviruses are endemic to Africa, Asia, Europe and Australia; they mostly cause arthritic disease and include: Sindbis virus (SINV), CHIKV, O'nyong-nyong virus (ONNV), Ross River virus (RRV), Barmah Forest virus (BFV) and Semiliki Forest virus (SFV). CHIKV infection causes an illness with symptoms that start 4-7 days after the mosquito bite. Schwartz, O. & Albert, M. L. Biology and pathogenesis of chikungunya virus. (See Nature reviews. Microbiology 8, 491-500, doi:10.1038/nrmicro2368 (2010).) Infection is presented in two phases, the first being acute while the second stage is persistent (chronic) causing prolonged arthralgic disease that affects the joints of the extremities. Most patients fully recover, but in 10% of the cases, joint pain may persist for several months or even years. Occasional cases of eye, neurological, and heart complications have been reported, as well as gastrointestinal complaints. The CHIKV mortality rate has been estimated to be 1:1000, and most of the deaths occur in neonates, adults with underlying conditions, and the elderly. (See Weaver, S. C. Arrival of chikungunya virus in the new world: prospects for spread and impact on public health. PLoS neglected tropical diseases 8, e2921, doi: 10.1371/journal.pntd.0002921 (2014).)

In particular, the CHIKV genome is a positive sense, single stranded RNA genome of about 11.8 kb in size. The alphavirus nonstructural protein nsP2 structure is organized into two domains and the C-terminal domain forms the papain-like protease. (See Sourisseau, M. et al. Characterization of reemerging chikungunya virus. PLoS pathogens 3, e89, doi:10.1371/journal.ppat.0030089 (2007); and Singh Kh, D. et al. Homology modeling, molecular dynamics, e-pharmacophore mapping and docking study of Chikungunya virus nsP2 protease. Journal of molecular modeling 18, 39-51, doi:10.1007/s00894-011-1018-3 (2012).) that cleaves the nsP1234 polyprotein, which contains the precursors to the four alphavirus non-structural proteins (nsP1-nsP4). The crystal structure of CHIKV nsP2 protease (nsP2pro) is available and it is a cysteine protease composed of 324 residues (PDB file 3TRK). The catalytic mechanism of cysteine proteases involves a nucleophilic cysteine thiol in a catalytic dyad. (See Rashad, A. A., Mahalingam, S. & Keller, P. A. Chikungunya virus: emerging targets and new opportunities for medicinal chemistry. *Journal of medicinal chemistry* 57, 1147-1166, doi:10.1021/jm400460d (2014).) Alphavirus nsP2pro is an attractive drug target for three reasons: (1) its activity is essential for virus replication; (2) it cleaves substrates with defined recognition sequences (Asp/Glu-Ala-Gly-Ala or Glu-Ala-Gly-Cys (SEQ ID NO: 1)); and (3) the active domain of nsP2pro is highly conserved for CHIKV, VEEV, and SINV. (See Russo, A. T., White, M. A. & Watowich, S. J. The crystal structure of the Venezuelan equine encephalitis alphavirus nsP2 protease. Structure 14, 1449-1458, doi:10.1016/j.str.2006.07.010 (2006); and Saisawang, C. et al. Chikungunya nsP2 protease is not a papain-like cysteine protease and the catalytic dyad cysteine is interchangeable with a proximal serine. Sci Rep 5, 17125, doi:10.1038/srep17125 (2015).

With recent outbreaks and expanding geographical ranges of human infectious alphaviruses, the lack of therapeutics presents a grave concern. Classical screening for anti-virals in cellular assays are prohibitively expensive and time-consuming. A rapidly deployable system that is readily amenable for high-throughput screening was used here to identify the compounds with activity against alphaviruses. A cloning step to substitute the sequence of the FRET linker was used to generate the new substrate, needing only addition of recombinant nsP2 protease to complete the in vitro assay. Recombinant protein production enables the two component system to be rapidly modified to interrogate newly emerging or re-emerging viruses, allowing for rapid discovery of lead anti-viral compounds.

With a high-throughput small-molecule library screen, some degree of false-positives is to be expected. By using a cell-free system, time and cost required for primary and secondary screening as a result of false positives was improved. Compounds that reduce fluorescence in cell-free conditions were further characterized in cellular assays to rule out drugs that were reactive, non-membrane permeable, or had off-target or direct cytotoxic effects, which generally are self-selected in cell-based screening assays. Nonetheless, not ruling out such compounds in the primary screen can be advantageous. Compounds that reduce recombinant in vitro protein activity can be used for in silico optimization studies, to generate compound analogs that are membrane permeable, non-cytotoxic and specific.

Figure 12:
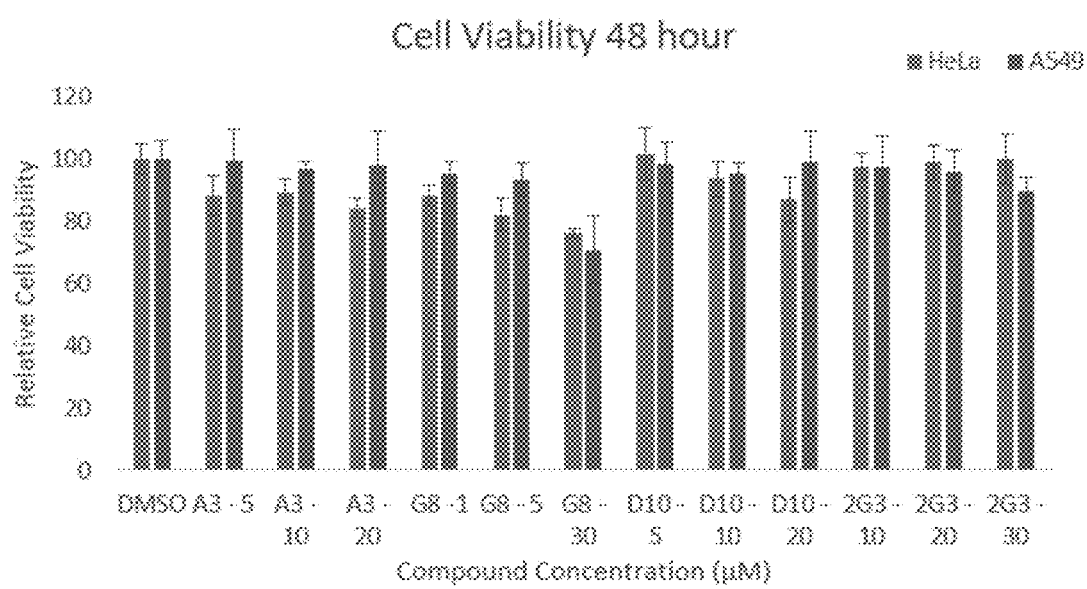
FIG. 12 is a bar graph showing relative percent infection of the four compounds of interest in HeLa and A549 cells of related alphavirus of the alphavirus Venezuelan Equine Encephalitis Virus at 48 hours.

Tissue culture lines, both primary and immortalized, exhibit a variety of different morphologies and responses, particularly to pathogen challenge. Cell lines are often chosen for initial studies due to their cost-effectiveness, homogeneity, and ease of transfection. Cell lines have been genetically altered to induce that immortalization, and these genetic changes could alter their phenotype, cell signaling processes and how they respond to stimuli (small molecules and/or pathogens). For example, two of the cell lines tested, HeLa (human papilloma virus-positive cervical cancer cell line) and 293 Ts (SV40 large T antigen-transformed embryonic kidney cell line), were transformed by viruses and therefore have different growth effects, and genetic alterations due to gene inactivation from viral proteins. The A549 cell line is a KRAS G12S-mutant lung cancer cell line that tends to be more refractory to virus infection due to a competent interferon alpha response. (See Shen, J. P. et al. Combinatorial CRISPR-Cas9 screens for de novo mapping of genetic interactions. *Nat Meth* 14, 573-576, doi:10.1038/nmeth.4225) (2017).) A few features may therefore impact efficacy of anti-viral compounds. First, the small-molecule compounds themselves may differentially interact with the line. This may explain the inherent cytotoxicity differences observed among multiple cell lines (See e.g., FIG. 12). Expression of different surface or cellular proteins may play a role, as do relative expression levels or signaling pathways.

The differences among various tissues lines is relevant to viral pathogenicity. Viral infectivity, titer, course of infection, and cytopathic effects can differ drastically in different cell types. Therefore, several independent avenues were utilized to better understand the anti-viral efficacy of these compounds. The CHIKV-GFP reporter virus allowed for rapid, convenient screening methodology of cellular assays in technical and biological replicates. Fusion to nsP3 results in stable expression of the GFP, albeit at relatively low levels—nsP3 has an estimated half-life of 45 minutes. However, nsP3 is part of the nonstructural polyprotein, that requires nsP2pro cleavage for expression. An additional advantage of the nsP3-GFP reporter is that it can be used to assess sub-cytopathic levels of viral infection at earlier time points. This is an important distinction, as there are many factors that influence viral spread in the host. A modest reduction in infectivity, in replication, or in cytopathic effect can have an unexpectedly large effect in concertion with the host immune system, as altering the exponential trajectory has large downstream impact.

One challenge of the CHIKV-GFP reporter virus is that it is challenging to determine whether the change in signal is due to reduced viral load per cell, or whether fewer cells show infection. Flow cytometry therefore was useful in determining whether the latter is a factor. One caveat is that antibodies used for cell labeling target the virus glycoproteins, which as part of the structural polyprotein are not subject to nsP2-mediated cleavage. Nonetheless, presence of the viral structural proteins can be due to newly infected cells, or cells producing structural proteins, and thus are suitable to assess the relative percentage of infection, which showed reduction of CHIKV in all four lead compounds.

It should be noted that detection of the nsP3-GFP fusion, or detection of the glycoproteins from the structural polyprotein, are not inherently representative of true viral levels, as proteins may be produced and detectable even without proper function or the ability to produce true infectious virions. Thus, such in vitro assays likely underrepresent the efficacy of anti-viral compounds. Therefore, assessing viral titers in the presence of compound-treated cells was utilized. In only 24 hours, CHIKV titers were reduced by approximately one log at higher concentrations.

Although the New World alphaviruses, including VEEV, evolved separately from those of the Old World alphaviruses, i.e., CHIKV, both groups share common characteristic in their replication strategies. Even though CHIKV nsP2 has a longer substrate sequence than VEEV nsP2, the crystal structure for both protease domains have been resolved and they are similar. (See Saisawang, C. et al. Chikungunya nsP2 protease is not a papain-like cysteine protease and the catalytic dyad cysteine is interchangeable with a proximal serine. *Sci Rep* 5, 17125, doi:10.1038/srep17125 (2015); and Russo, A. T. & Watowich, S. J. Purification, crystallization and X-ray diffraction analysis of the C-terminal protease domain of Venezuelan equine encephalitis virus nsP2. *Acta Crystallogr Sect F Struct Biol Cryst Commun* 62, 514-517, doi:10.1107/S1744309106014667 (2006).) Thus, with the disclosure herein that the compounds that strongly inhibit CHIKV nsP2 also appear to have efficacy against VEEV in cell culture, it should indicate antiviral activity against other alphaviruses as well.

Figure 15:
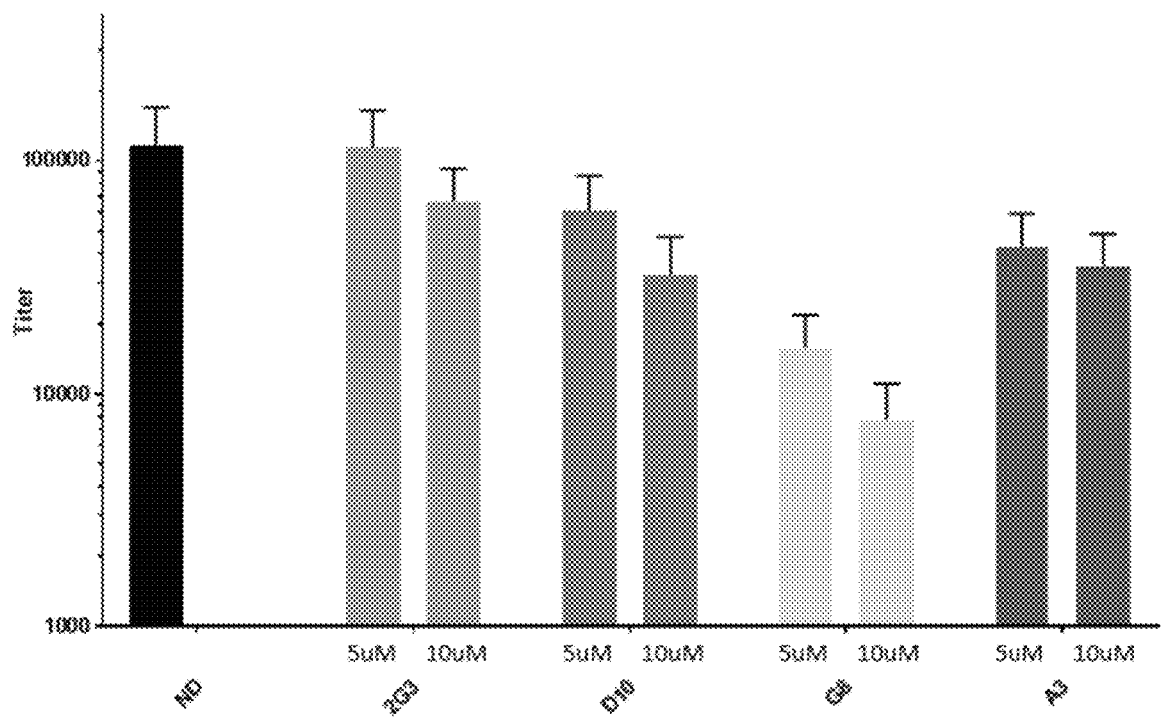
FIG. 15 is a bar graph showing viral titers of Zika virus measured in the presence of the compounds of interest.

The finding that one compound, Compound IV, worked on additional viruses such as Zika, and specifically Rift Valley Fever Virus is particularly unexpected, owing to the distance between bunyaviruses and alphaviruses and the lack of a viral protease. As Compound IV showed varied efficacy amongst different cell types, it's possible that the anti-viral properties being observed are due to some off-target effects or interactions. In the time of addition assay (See FIG. 15), Compound IV was the only compound to show consecutively reduced levels of efficacy at later time-points, suggesting a role in either early viral replication or cellular entry. Compound IV may act in a host-directed manner, thus enabling a broader anti-viral effect.

In an embodiment, cytotoxicity of the compounds corresponds to an IC50 of less than 50 µM against an alphavirus, such as less than 25 µM, or from 15 µM to 2 µM. With respect to CHIKV-GFP, compounds III and IV had the lowest projected IC50 values of 2.82 uM, and 2.59 uM respectively, while the IC50 of compound I was 10.88 uM, and the IC50 of compound II was 4.9 uM.

Pharmaceutical compositions including the compounds disclosed herein may include an effective amount of the compound or compounds formulated to affect a therapeutic result. In an embodiment, the compound or compounds are formulated in combination with a pharmaceutically acceptable carrier, additive or excipient. Pharmaceutical compositions disclosed herein may also comprise an additional bioactive agent or drug, such as a symptom treating drug, e.g., pain reliever, fever reliever, inflammation reliever, antihistamine, decongestant, or a secondary antiviral agent. In an embodiment, the additional active agent is targeted for therapy of an alphavirus.

Generally, dosages and routes of administration of the compound are determined according to the size and condition of the subject, according to standard pharmaceutical practices. A therapeutically effective amount should be used; and, typically, amounts in the milligram/microliter up to gram/milliliter quantities are employed with the active compounds being used in the range of concentrations of the whole pharmaceutical compound as disclosed below. For example, for a human subject, 1 mg to 2 g of the pharmaceutical compound may be formulated for one dose, such as, for example, 3 mg to 1 g, or 5 mg to 0.5 mg for an oral dosage in pill or suspension form. Other delivery mediums, such as dissolvable strips or parenteral formulations, may have dosages derived from these ranges given the adjustments for concentrations and other factors known to those of skill in the art.

The composition may be administered to a subject by various routes, e.g. orally, transdermally, perineurally or parenterally, that is, by intravenous, subcutaneous, intraperitoneal, intrathecal or intramuscular injection, among others, including buccal, rectal and transdermal administration. However, given the water solubility of the small molecule compounds, oral preparations and delivery is likely to be preferable.

Subjects contemplated for treatment according to the methods and compounds disclosed herein include humans and animals. The pharmaceutical composition contemplates immediate and/or sustained/controlled release compositions, including compositions which comprise both immediate and sustained release formulations. This is particularly true when secondary actives are used in the pharmaceutical compositions.

Formulations containing the compounds disclosed herein may take the form of liquid, solid, semi-solid or lyophilized powder forms, such as, for example, solutions, suspensions, emulsions, sustained-release formulations, tablets, capsules, powders, suppositories, creams, ointments, lotions, aerosols, patches or the like, preferably in unit dosage forms suitable for simple administration of precise dosages.

Pharmaceutical compositions including the compounds disclosed herein may include a conventional pharmaceutical carrier or excipient and may additionally include other medicinal agents, carriers, adjuvants, preservatives, and/or additives. In an embodiment, the pharmaceutical composition contains 0.1% to 95%, 0.5% to 75%, or 1 to 50% by weight of a compound or compounds disclosed herein, with the remainder consisting essentially of suitable pharmaceutical excipients.

An injectable composition for parenteral administration (e.g. intravenous, intramuscular or intrathecal) will typically contain the compound in a suitable IV solution, such as sterile physiological salt solution. The composition may also be formulated as a suspension in an aqueous emulsion.

Liquid compositions can be prepared by dissolving or dispersing the compound (e.g. 0.5% to 80% by weight, 1% to 70%, or 5% to 20% by weigh), and optional pharmaceutical adjuvants, in a carrier, such as, for example, aqueous saline, aqueous dextrose, glycerol, or ethanol, to form a solution or suspension. For use in an oral liquid preparation, the composition may be prepared as a solution, suspension, emulsion, or syrup, being supplied either in liquid form or a dried form suitable for hydration in water or normal saline.

For oral administration, such excipients include, for example, pharmaceutical grades of mannitol, lactose, starch, magnesium stearate, sodium saccharine, talcum, cellulose, glucose, gelatin, sucrose, and magnesium carbonate. If desired, the composition may also contain minor amounts of non-toxic auxiliary substances such as wetting agents, emulsifying agents, or buffers.

When the composition is employed in the form of solid preparations for oral administration, the preparations may be tablets, granules, powders, capsules or the like. In a tablet formulation, the composition is typically formulated with additives, e.g. an excipient such as a saccharide or cellulose preparation, a binder such as starch paste or methyl cellulose, a filler, a disintegrator, and other additives typically used in the manufacture of medical preparations.

Methods of treating patients or subjects in need for an alphavirus, such as those disclosed herein, comprise administration an effective amount of a pharmaceutical composition comprising the compounds disclosed herein and optionally at least one additional bioactive (e.g. antiviral) agent according to the present disclosure.

In an embodiment, the pharmaceutical preparation can be taken one to six times per day, such as two to three times per day, or three to four times per day. The dosage regiment may be continued for 1 to 14 days, 2 to 10 days, or 3 to 7 days, or otherwise as long as symptoms persist, or testing shows that an infection is still present.

The following non-limiting examples are illustrative of the invention and its advantageous properties and are not to be taken as limiting the disclosure or claims in any way. In the examples, as well as elsewhere in this application, all parts and percentages are by weight unless otherwise indicated.

EXAMPLES

Summary of Examples and Material and Conditions Information

In order to exploit nsP2pro as target for inhibition, an in vitro assay to monitor substrate cleavage using a fluorescence resonance energy transfer (FRET) based substrate was designed. FRET relies on distance-dependent transfer of energy from a donor molecule to an acceptor molecule. Two recently engineered fluorescent proteins, Clover and mRuby2, have been described as the brightest green and red fluorescent proteins to date and have the highest Förster radius of any ratiometric FRET pair yet described (See Boute, N., Jockers, R. & Issad, T. The use of resonance energy transfer in high-throughput screening: BRET versus FRET. *Trends Pharmacol Sci* 23, 351-354 (2002); Lam, A. J. et al. Improving FRET dynamic range with bright green and red fluorescent proteins. *Nat Methods* 9, 1005-1012, doi:10.1038/nmeth.2171 (2012).) By fusing these proteins using the CHIKV nsP2pro substrate sequence as a linker, a rapidly deployable assay was developed that was amenable for high-throughput screening (HTS) of existing small-molecule libraries.

A small-molecule library of 40,000 compounds, provided by the UCLA MSSR, was screened using this assay, with a z' of 0.53. The top 320 hits that showed ≥80% inhibition were selected for secondary-screening and 101 compounds were validated. These compounds were tested in cells for cytotoxicity and anti-viral efficacy against CHIKV-GFP reporter virus infection and the four compounds of structures I-IV disclosed above were identified.

The compounds were further characterized within different cell types, using multiple methods to measure virus infection (flow cytometry, plaque reduction assays, and time of addition assays) and different virus strains to determine the spectrum of activity. These compounds (I-IV) inhibited CHIKV replication in a dose dependent manner and demonstrated activity against the new world alphavirus VEEV. Compound IV was effective against a diverse set of viruses, including bunyaviruses, flaviviruses and alphaviruses without being cytotoxic.

All cell lines were maintained in culture medium supplemented with 10% fetal bovine serum (FBS), 100 units/ml penicillin, and 100 g/ml streptomycin (Thermo Fisher) at 37° C. in 5% $CO_2$. HeLa cells (human cervix carcinoma), BHK21cells (baby hamster kidney fibroblasts), and 293T (human embryonic kidney) cells were cultured in Dulbecco's modified Eagle's medium (DMEM), while Vero cells (African green monkey kidney) were maintained in Minimum Essential Media Alpha medium, and A549 cells (human lung epithelial) were cultured in F-12K medium.

Example 1: Production of Recombinant Proteins

The FRET protein substrate was obtained from Addgene (#49089) and cloned into a pET expression vector (pET30b)

for bacterial expression. The CHIKV nsP2/3 protease substrate sequence was synthesized by IDT and cloned in-between the two reporter proteins. CHIKV nsP2pro was synthesized as a gene block using IDT and cloned into the pDEST-HisMBP vector from Addgene (#11085). These vectors were than transformed into BL21DE3 expression-*E. coli* (NEB). Cultures were grown and protein was purified following established protocols using the 6×His tag (SEQ ID NO: 2) over Ni-NTA Agarose resin (Qiagen) 26-29. Protein purity and activity was determined using spectrophotometers, protein gel staining, and optimization assays.

Example 2: In Vitro nsP2 Cleavage Assay

The assay was optimized for 384-well format using the M1000 Infinity Plate Reader (Tecan). In short, 50 ul reactions containing 5 ug of MBP-nsP2protease (~1.33 uM) and 2 ug of FRET substrate (~800 nM) were incubated overnight in reaction buffer at room temperature. The reaction buffer was composed of 50 mM TRIS, 150 mM NaCl, pH 7.4. After incubation, plates were read on fluorescent plate readers with excitation at 470 nM, and emission gathering at 518 nM (Clover) and 586 nM (FRET induced emission of mRuby2). Analysis was performed using Microsoft Excel, by setting the Clover:mRuby2 of uncleaved substrate as 1.00, allowing for assessment of cleavage by an increase of the Clover to mRuby2 emission ratios, which also allowed for normalization of substrate amount per well.

Example 3: High-Throughput Screening and Analysis

High-throughput screening was performed at UCLA's Molecular Screening Shared Resource (MSSR) center, a core facility. The 40,000 compound "LS" library that was selected is a diverse smart library, selected from larger compound sets based on computational clustering and analysis to allow for sampling of larger, diverse pools of compounds. (See Damoiseaux, R. UCLA's Molecular Screening Shared Resource: enhancing small molecule discovery with functional genomics and new technology. Comb Chem High Throughput Screen 17, 356-368 (2014), incorporated herein by reference.)

A Multidrop 384 (Thermo Lab Systems) was used for liquid handling. In brief, 25 µl of either buffer or MBP-nsP2 in reaction buffer was dispensed to all wells. A BioMek FX liquid handler pinned 50 nl of compound libraries or DMSO controls to each plate. Following incubation of 30 min to 1 hour, the multidrop liquid handler was used to dispense 25 µl of FRET substrate in reaction buffer to all wells. Each plate consisted of two rows of FRET-substrate incubated with DMSO (32 wells), 20 rows (320 wells) of 10 µM compound-incubated MBP-nsP2 and FRET substrate, and two rows of DMSO-incubated MBP-nsP2 and FRET substrate (32 wells). This provided 32 wells to serve as "no cleavage" and "maximum cleavage" controls for downstream normalization. Plates were sealed using aluminum film, incubated, and then unsealed and read on an Analyst GT Multimode plate reader (Molecular Devices) for fluorescence as described above, using automation and plate stackers. Output was analyzed using Microsoft Excel as described above, and GraphPAD Prism for statistical analyses. Secondary screening was performed in a similar fashion, excepting that the 320 compounds from the primary screen were arrayed manually into a single 384-well source plate.

Example 4: Visualization of Protein Gels

Independent assessment of protease cleavage was done by taking the reaction samples, adding commercial Laemmli Sample Buffer (BioRad), and boiling at 95*C for 10 minutes. Denatured protein was then loaded into an 8-16% gradient acrylamide gel following manufacturer's protocols (BioRad). The gel was washed in water and stained using Coomassie-SafeStain following the manufacturer's protocols (ThermoFisher). (See Zehr, B. D., Savin, T. J. & Hall, R. E. A one-step, low background coomassie staining procedure for polyacrylamide gels. *Analytical biochemistry* 182, 157-159 (1989) incorporated herein by reference.) The stained gel was imaged using the colorimetric setting on an AlphaImager machine.

Example 5: Virus

Chikungunya virus vaccine strain 181/25 (CHIKV 181/25) was obtained. (See Gorchakov, R. et al. Attenuation of Chikungunya virus vaccine strain 181/clone 25 is determined by two amino acid substitutions in the E2 envelope glycoprotein. *Journal of virology* 86, 6084-6096, doi: 10.1128/jvi.06449-11 (2012), incorporated herein by reference.) Venezuelan Equine Encephalitis Virus, TC-83, NR-63 was obtained through the NIH Biodefense and Emerging Infections Research Resources Repository, NIAID, NIH. The recombinant RVFV vaccine strain MP12 generated to carry a green fluorescent protein (GFP) gene (RVFV MP12-GFP) in place of the NSs gene has been described previously. (See Harmon, B. et al. Rift Valley fever virus strain MP-12 enters mammalian host cells via caveola-mediated endocytosis. *J. Virol.* 86, 12954-12970 (2012) incorporated herein by reference.) Authentic nonrecombinant RVFV strain MP12 was obtained from the University of Texas Medical Branch. (See Caplen, H., Peters, C. J. & Bishop, D. H. Mutagen-directed attenuation of Rift Valley fever virus as a method for vaccine development. The Journal of general virology 66 (Pt 10), 2271-2277 (1985) incorporated herein by reference; and Ikegami, T., Won, S., Peters, C. J. & Makino, S. Rescue of infectious rift valley fever virus entirely from cDNA, analysis of virus lacking the NSs gene, and expression of a foreign gene. Journal of virology 80, 2933-2940, doi:10.1128/JVI.80.6.2933-2940.2006 (2006) incorporated herein by reference.)

Concentrations of plaque forming units for all viruses were quantified in Veros using a standard plaque assay consisting of an agarose overlay with crystal violet staining. (See Baer, A. & Kehn-Hall, K. Viral concentration determination through plaque assays: using traditional and novel overlay systems. *Journal of visualized experiments: JoVE*, e52065, doi:10.3791/52065 (2014) incorporated herein by reference.) For CHIKV-GFP reporter assays, virus was added at a MOI of 1.0 to pre-incubated compounds and analyzed at either 24 or 48 hours. For CHIKV 181/25, VEEV, RVFV, and ZIKV assays, cells were pretreated with compounds for 30 min to 1 hour, and then inoculated with virus for three hours. After three hours, cells were washed once with PBS, and then incubated with compound-treated media at the indicated concentrations. The time of addition assay was performed similarly, except virus incubation was only two hours, and cells were only pre-treated or treated with compound post-infection.

Example 6: Generation of CHIKV-nsP3 Reporter Viruses

The infectious clone plasmid pSinRep5-181/25ic was obtained from Addgene (#60078). A CRISPR/Cas9 digest reaction using the sgRNA guide sequence of CAAGGTTTCCGATTATGGT (SEQ ID NO: 3) was performed, using in house produced Cas9 and guide RNA following established protocols. (See Zuris, J. A. et al. Cationic lipid-mediated delivery of proteins enables efficient protein-based genome editing in vitro and in vivo. Nature biotechnology 33, 73-80, doi:10.1038/nbt.3081 (2015) incorporated herein by reference; and Wang, J. W. et al. CRISPR/Cas9 nuclease cleavage combined with Gibson assembly for seamless cloning. BioTechniques 58, 161-170, doi:10.2144/000114261 (2015), incorporated herein by reference.) This was done to linearize the plasmid in the region of nsP3 previously targeted for reporter integration. (See Sun, C., Gardner, C. L., Watson, A. M., Ryman, K. D. & Klimstra, W. B. Stable, high-level expression of reporter proteins from improved alphavirus expression vectors to track replication and dissemination during encephalitic and arthritogenic disease. *Journal of virology* 88, 2035-2046, doi:10.1128/jvi.02990-13 (2014), incorporated herein by reference).

DNA for both eGFP and mCherry was synthesized as a gBlock from IDT, Inc, and was ligated into the linearized vector using Gibson cloning (NEB). Plasmid sequences were verified by Sanger sequencing (Quintara Bio), and the plasmid was linearized with Not1 restriction digest enzyme (NEB). mRNA was produced and purified following manufacturer's protocols using the mMessage mMACHINE kit and MEGAclear RNA transcription clean-up kit (Thermo Fisher). Viral mRNA was transfected into BHK21 cells following manufacturer's protocols using Lipofectamine 3000 (Thermo Fisher). Virus was passaged four times in BHK21 cells to reduce quasispecies, before supernatant was harvested, filtered through a 0.22 micron syringe filter (Fisher), and frozen in single use aliquots at −80° C.

Example 7: Cellular Viability and Fluorescence Assays

Cell viability was measured using Presto Blue Cell Viability Reagent (ThermoFisher Scientific), according to the manufacturer protocol. Briefly, cells were plated overnight in complete media in 96 well plate at $1\times10^4$ cells per well. Cells were treated with inhibitors and/or virus for indicated time periods prior to determining cell viability. Presto Blue Cell Viability Reagent was added to cells in complete media to make a 1× final concentration and cells were incubated for 15 min at 37° C. Fluorescence was measured at EX535/EM615 using the Tecan M1000 Infinity Plate Reader (Tecan). Assay plates were then washed three times with PBS using a BioTek EL406 plate washer, and GFP fluorescence was measured at EX488/EM510 using the M1000 Infinity Plate Reader. PBS was aspirated, and cells were incubated with commercial RIPA Lysis Buffer (ThermoFisher), subjected to a freeze and thaw cycle at −20*C and 37*C respectively, and then measured again for total fluorescence. Analysis of data was done using Microsoft Excel and GraphPAD Prism for graphing and statistical analyses. These experiments were performed in triplicate 3 or more times and the average (±standard deviation) of three independent experiments was determined.

Example 8: Flow Cytometry and Analysis

After experimental treatments, cells were washed with PBS prior to EDTA-trypsin treatment (Invitrogen) to remove cells from the plate. Cells were washed in PBS again and fixed with 4% PFA for 30 min on ice before being resuspended into PBS with 100 mm glycine. Cells were then incubated with the appropriate antibody per virus type in a permeabilization buffer (PBS containing 0.1% saponin, 20 mM EDTA, 0.02% and 2% FBS for 1 hour) with rotation at 4° C. Primary antibodies include the following: IgG and IgM antibodies against VEEV antigen (VEEV VR69 ATCC) at 1:500; anti-RVFV mouse polyclonal antibody (provided by Robert Tesh at UTMB) at 1:500; and anti-CHIKV mouse monoclonal antibody 3585 (AbCam) at 1:50. After incubation with primary antibody, cells were washed with PBS, and incubated with goat anti-mouse antibodies coupled to AlexaFluor488 (Invitrogen) for 30 min at 4° C. Cells were washed again, and then analyzed using an Accuri C6 Plus flow cytometer (BD Biosciences). Cells were counted as infected if their fluorescence was greater than that of DMSO treated uninfected cells. Data analysis was performed using FCS Express 5 Flow Cytometry Data Analysis software (De Novo Software). Uninfected cells were similarly probed with primary and secondary antibody to control for any nonspecific binding.

Example 9: Small Molecule Compounds

After identification through the Assay examples above, the small-molecule compounds I-IV were obtained through Life Sciences, and were resuspended into DMSO (Sigma) at 10 mM concentrations. The compounds were diluted into the cell media appropriate relative to the cell line being used, at the final concentrations as indicated in the figures.

Example 10: An In Vitro High-Throughput Screening Assay to Identify Inhibitors of CHIKV nsP2pro CHIKV's single strand, positive-sense RNA genome, is comprised of two open reading frames. (Pietila, M. K., Hellstrom, K. & Ahola, T. Alphavirus polymerase and RNA replication. Virus research 234, 44-57, doi:10.1016/j.virusres.2017.01.007 (2017) incorporated herein by reference.) The first encodes the nonstructural polyprotein, containing nsP1, P2, P3, and P4, and the second contains the viral structural proteins. Processing of the nsP1234 polyprotein is mediated by nsP2pro, with cleavage of nsP3/4 occurring early and cleavage of nsP1/2 followed by nsP2/3 occurring later in the viral replication cycle (See FIG. 1). (See Jose, J., Snyder, J. E. & Kuhn, R. J. A structural and functional perspective of alphavirus replication and assembly. Future Microbiol 4, 837-856, doi:10.2217/fmb.09.59 (2009); Rupp, J. C., Sokoloski, K. J., Gebhart, N. N. & Hardy, R. W. Alphavirus RNA synthesis and non-structural protein functions. The Journal of general virology 96, 2483-2500, doi:10.1099/jgv.0.000249 (2015); and Bhakat, S., Karubiu, W., Jayaprakash, V. & Soliman, M. E. A perspective on targeting non-structural proteins to combat neglected tropical diseases: Dengue, West Nile and Chikungunya viruses. European journal of medicinal chemistry 87, 677-702, doi:10.1016/j.ejmech. 2014.10.010 (2014) incorporated herein by reference.)

Figure 1:
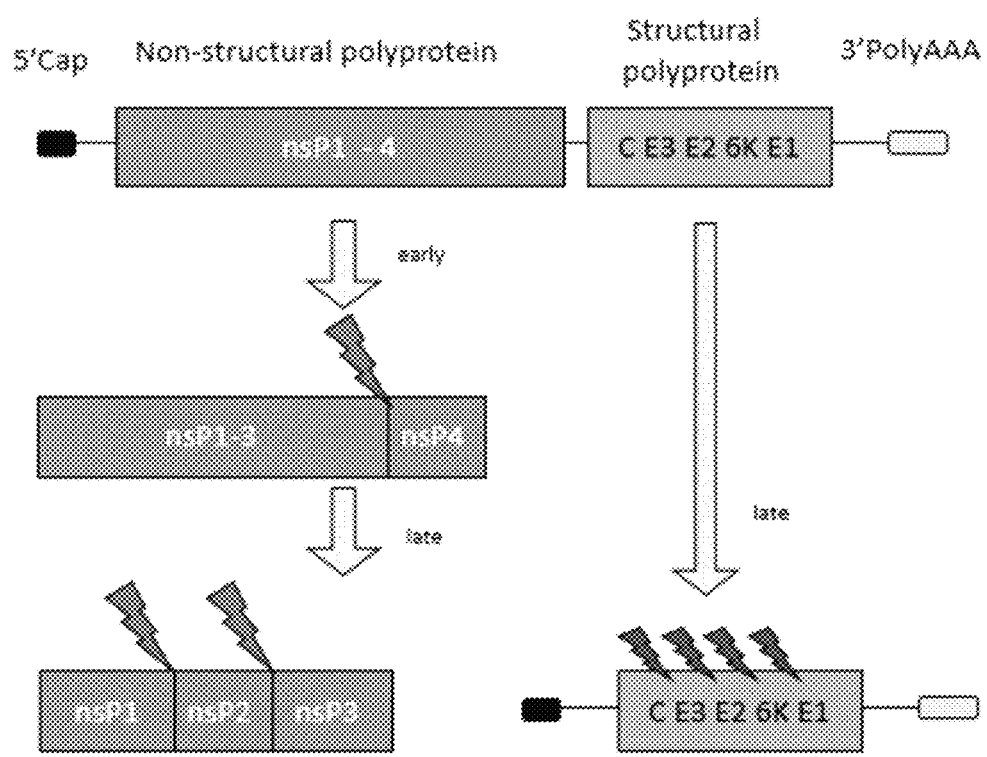
FIG. 1 is a graphic showing processing of the nsP1234 polyprotein mediated by nsP2pro, with cleavage of nsP3/4 occurring early and cleavage of nsP1/2 followed by nsP2/3 occurring later in the viral replication cycle

With further reference to FIG. 1, chikungunya has an approximately 11.8 kb, positive-sense RNA genome, comprised of a 5'cap structure, a 3' polyadenosine tail, and two open reading frames. The first encodes a nonstructural polyprotein, containing nsP1, P2, P3, and P4. The second contains the structural proteins, C2, E3, E2, 6K, and E1. After translation of nsP1234, cleavage of the polyprotein is done by the nsP2 protease, with cleavage events (red arrow), occurring either early or late in the replication cycle. Cleavage of nsP3/P4 can occur in cis or trans, whereas P1/P2 junction is in cis only. The final cleavage event is between nsP2/3. Cleavage of the structural polyprotein constituents occurs through different means, such as by capsid, by furin, or by signal peptidase. These required cleavage events provide an avenue to exploit nsP2pro as a target for anti-viral inhibitors.

To identify small molecule inhibitors of nsP2pro, an in vitro cell-free assay was developed utilizing recombinant nsP2pro in conjunction with a FRET-enabled substrate (FIG. 2). Using the nsP2pro cleavage substrate sequence as a linker between the Clover and mRuby2 fluorescent protein pairing (see Lam, A. J. et al. Improving FRET dynamic range with bright green and red fluorescent proteins. Nat Methods 9, 1005-1012, doi:10.1038/nmeth.2171 (2012)), excitation of Clover at 470 nM allows for indirect excitation of mRuby2 at 518 nm, resulting in emission of mRuby2 at 586 nm. With the addition of recombinant nsP2pro, the linker is cleaved, resulting in a loss of the FRET-induced mRuby2 excitation.

This two-component system was optimized for small-scale reactions, allowing for high-throughput screening to identify inhibitors of nsP2pro. An HTS was performed with a 40,000 compound small molecule library at 10 µM (FIG. 3) to assess inhibition of nsP2pro activity. FIG. 3 (top graph) shows the 40,000 compounds that were used in high-throughput screening and their percent cleavage. Changes in the Clover:mRuby2 fluorescence ratios were normalized against DMSO-treated controls and plotted as a percentage of relative cleavage. The top 1,000 compounds (box, lower graph) reduced FRET emission to below 50% of controls, indicating inhibition of nsP2pro cleavage activity.

Figure 4:
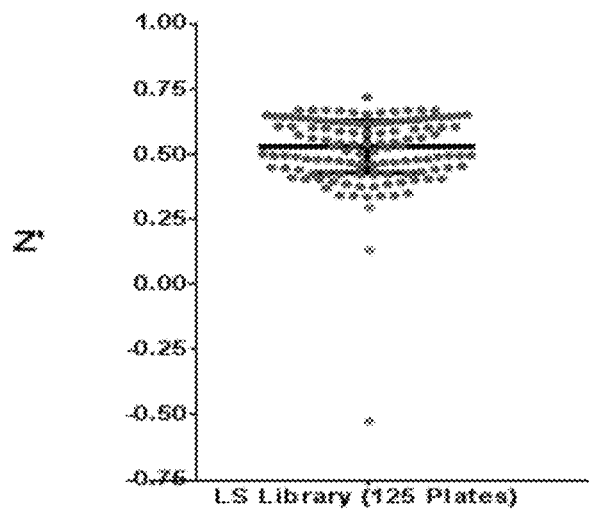
FIG. 4 is a plot showing a Z factor score per plate of the 384-well format compound library.

The 40,000 compound library was spread amongst 125 384-well plates, and 122 plates surpassed a quality z' threshold of 0.3. FIG. 4 shows the Z factor score per plate of the 384-well format compound library. Plates surpassing the 0.3 Z' threshold (blue) averaged to 0.53±0.10. Plates below the quality threshold (red) were excluded from subsequent analyses.

Over 1,000 compounds reduced FRET remission by 50% compared to controls in the primary screen. Hits from FRET-emission screening were verified by SDS-PAGE analysis of relative abundance of the substrate cleavage products. 320 compounds from the initial screen were chosen for secondary screening and arrayed into a single plate.

Figure 5:
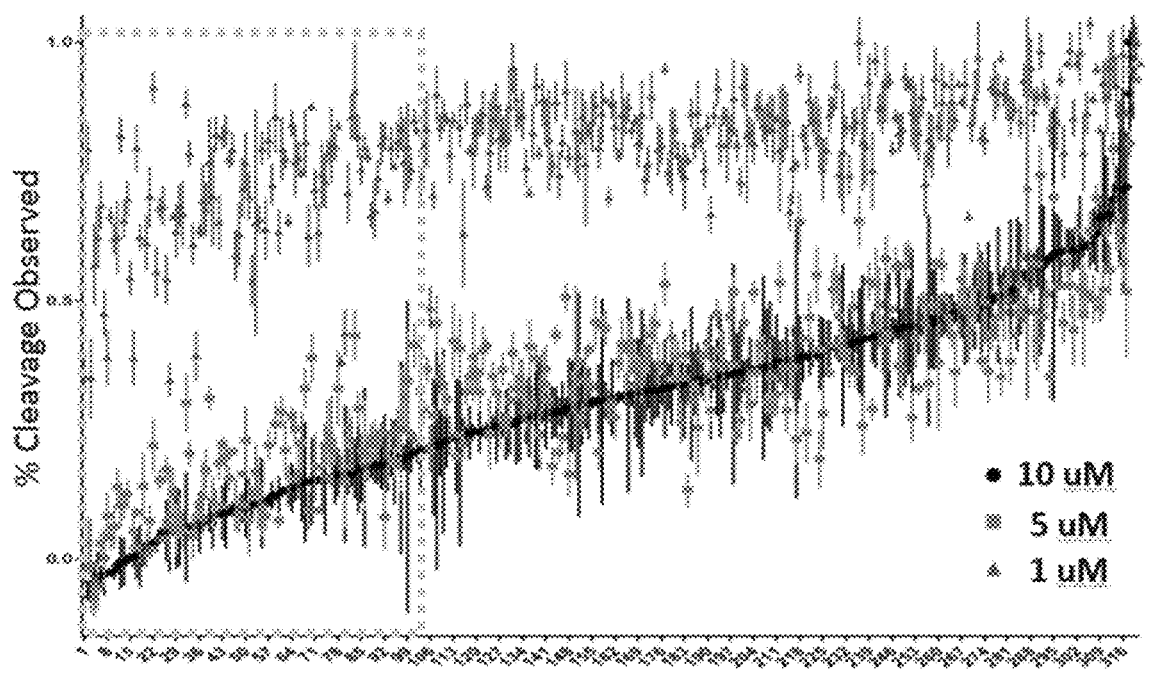
FIG. 5 is a plot of 320 compounds at three different concentrations showing percentage cleaved relative to DMSO-treated controls based on FRET fluorescence ratios.

These compounds were then assessed at three different concentrations: 10 µM in duplicate, 5p M in triplicate, and 1 µM in triplicate. FIG. 5 shows analysis of these compounds at the three different concentrations plotted as percentage cleaved relative to DMSO-treated controls based on FRET fluorescence ratios. The top compounds (encircled in a dotted square) were chosen for subsequent analyses. After secondary screening, the top 101 compounds demonstrating significant inhibition of nsP2pro in vitro were chosen for further studies.

Example 11: Determining Anti-CHIKV Efficacy of Candidate Compounds in Tissue Culture Screening Assays Small molecule libraries are known to contain a wide-variety of molecule types, including many which that are non-membrane permeable, cytotoxic, non-specific in functionality, or other attributes that may impair anti-viral efficacy in a cellular system. Therefore, the top 101 compounds from the screen were assessed for cytotoxicity in cell culture (data not shown).

Inhibitor-induced and virus-induced cell death can be determined using the cell viability indicator PrestoBlue. When added to cells, the reducing environment of viable cells changes the color of the reagent to a highly fluorescent red which can be measured at EX535/EM615. However, inhibitors with background fluorescence or cytopathic effects independent of virus infection can skew results when cell viability is monitored to determine levels of virus infection. In addition, CHIKV-induced cytopathic effects vary among different cell types. Human epithelial cells are generally refractory to CHIKV infection, with minimal cytopathic effect, though remerging CHIKV viral strains show increased infectivity and pathogenicity. (See Sourisseau, M. et al. Characterization of reemerging chikungunya virus. PLoS pathogens 3, e89, doi:10.1371/journal.ppat.0030089 (2007).)

In addition, it takes a minimum of 48 hours to detect a significant decrease in PrestoBlue fluorescence due to CHIKV infection. To facilitate initial screening of compounds for anti-viral efficacy in cells, a CHIKV 181/25 reporter virus was generated that expresses GFP upon entry and replication.

Figure 6:
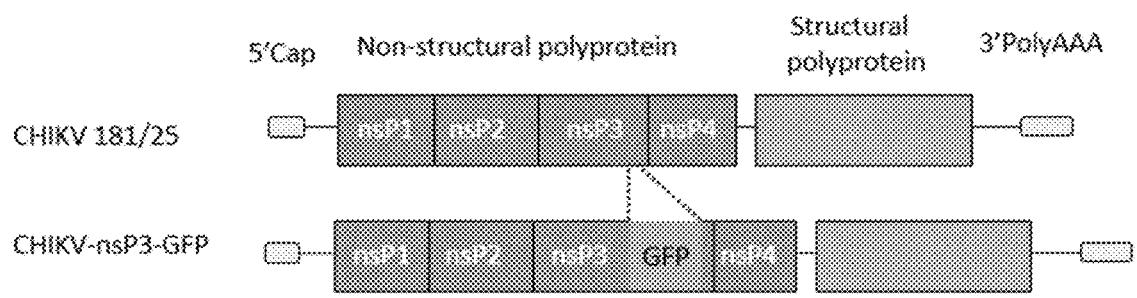
FIG. 6 is a graphic showing the CHIKV-nsP3-GFP viral genome. GFP is cloned into the C-terminal end of nsP3.

FIG. 6 illustrates the CHIKV-nsP3-GFP viral genome. GFP is cloned into the C-terminal end of nsP3. Fusing GFP to the nsP3 protein results in a stable, non-attenuated virus (CHIKV-GFP), and GFP expression serves as a sensitive readout of viral infection at early time points (24 hours) before virus-induced cell death can be measured by Presto-Blue assay. (See Sun, C., Gardner, C. L., Watson, A. M., Ryman, K. D. & Klimstra, W. B. Stable, high-level expression of reporter proteins from improved alphavirus expression vectors to track replication and dissemination during encephalitic and arthritogenic disease. Journal of virology 88, 2035-2046, doi:10.1128/jvi.02990-13 (2014).) CHIKV-GFP can be utilized in 96-plate tissue cultures format, allowing for rapid assessment of biological and technical replicates on standard plate readers. Additionally, a CHIKV-nsP3-mCherry variant (data not shown) was generated, as mCherry has greater tissue penetrance than GFP and would therefore have higher utilization in in vivo infections and imaging applications. (See Deliolanis, N. C. et al. In vivo tomographic imaging of red-shifted fluorescent proteins. Biomedical optics express 2, 887-900, doi:10.1364/boe.2.000887 (2011); and Heppert, J. K. et al. Comparative assessment of fluorescent proteins for in vivo imaging in an animal model system. Molecular biology of the cell 27, 3385-3394, doi:10.1091/mbc.E16-01-0063 (2016).)

Figure 7:
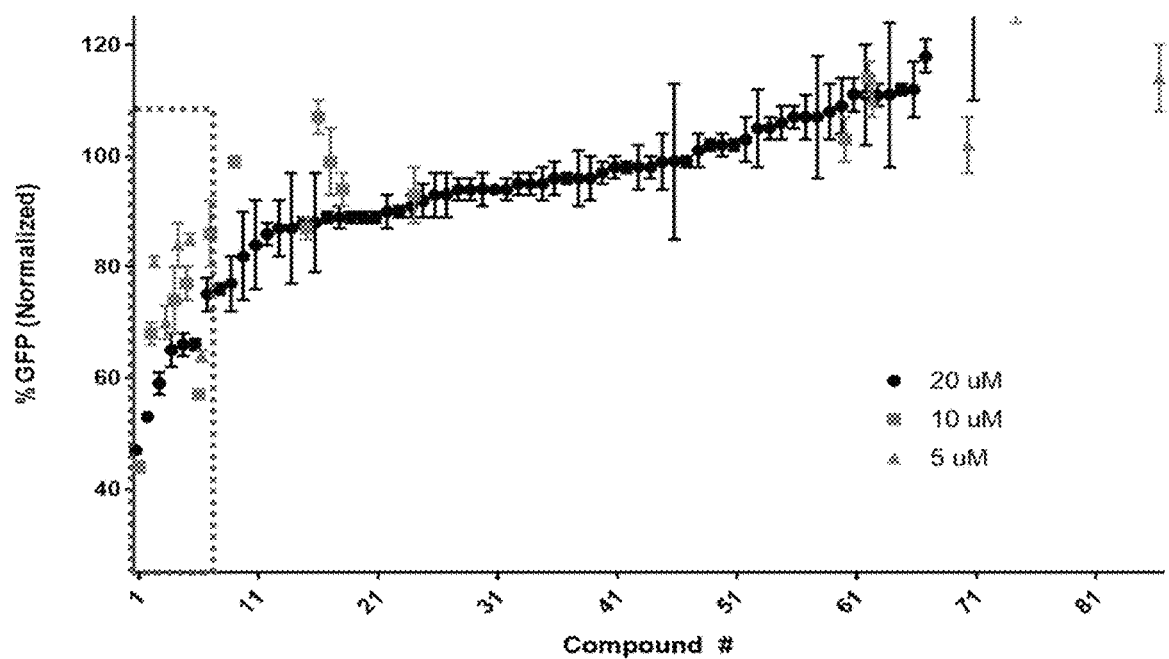
FIG. 7 is a plot showing compounds screened against CHIKV-GFP reporter virus, at 5, 10, or 20 uM concentrations

Utilizing the CHIKV-GFP reporter virus, the compounds were screened for reduction of virus dependent GFP fluorescence in CHIKV-GFP infected cells. FIG. 7 shows compounds that were screened against CHIKV-GFP reporter virus, at 5, 10, or 20 uM concentrations. Compounds inhibiting CHIKV-GFP to below DMSO-treated controls at 20 uM are plotted relative to inhibitory effect. Compounds exhibiting severe cytotoxicity or excessive background fluorescence were removed from analyses (data not shown). Out of about 101 compounds, very few were non-cytotoxic and effective at decreasing CHIKV-GFP infection, see square in dotted lines on FIG. 7. However, four compounds with structural formulas I-IV, significantly and reproducibly reduced virus-induced GFP fluorescence in HeLa cells.

Figure 8:
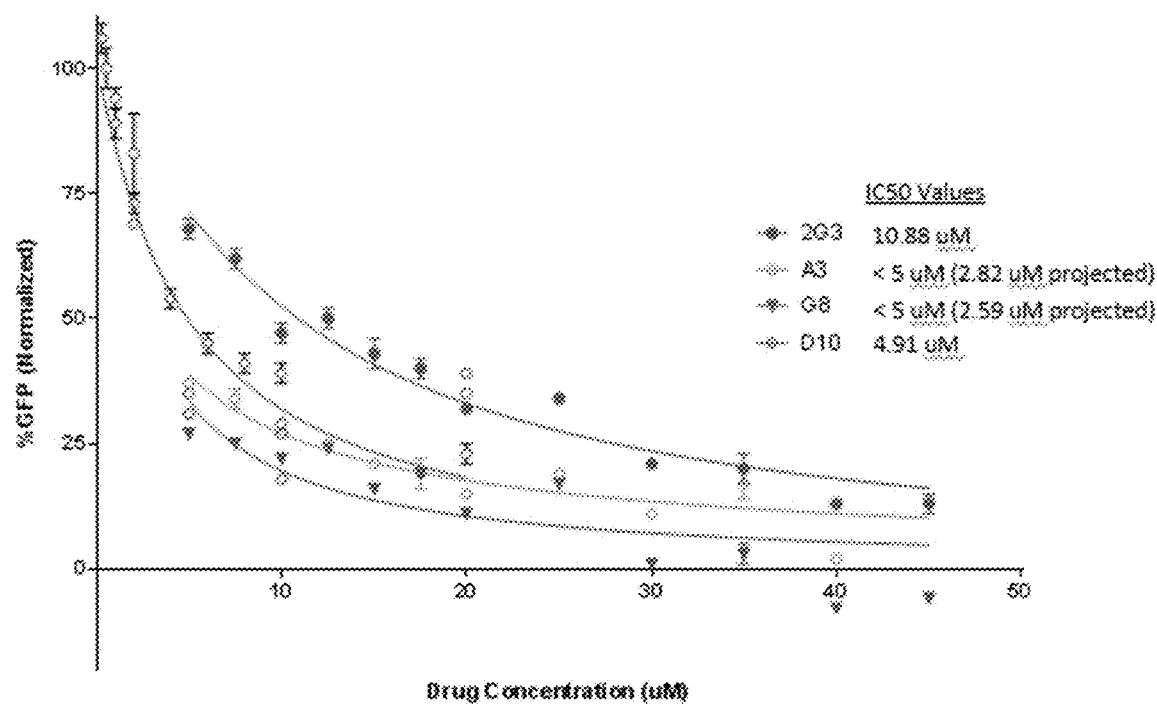
FIG. 8 is a plot showing compound efficacy against CHIKV-GFP reporter virus by compound IC50 values.

In FIG. 8, the anti-viral efficacy at a variety of concentrations was measured for these four compounds in HeLa cells to generate an IC50 dose response curve for each inhibitor. In FIG. 8, compound efficacy was assessed in triplicates per dosage, and treated cells were infected with CHIKV-GFP reporter virus. GFP values were normalized against DMSO-treated controls. The IC50 of each compound was determined using a nonlinear regression curve fitting, using an inhibitor vs normalized response w/variable slope analysis.

Based on the curve fitting, compounds III and IV had the lowest projected IC50 values of 2.82 uM, and 2.59 uM, respectively, while the IC50 of compound I was 10.88 uM, and the IC50 of compound II was 4.9 uM. As mentioned above, one of the benefits of the CHIKV-GFP reporter virus is that it facilitates determination of compound effectiveness in cell lines that show reduced cytopathic effects, such as human lung epithelial cells (A549 cell line). Based on the IC50 dose response curves in FIG. 8, three concentrations of each compound were evaluated in HeLa and A549 cells infected with CHIKV-GFP for 24 hours.

Figure 9:
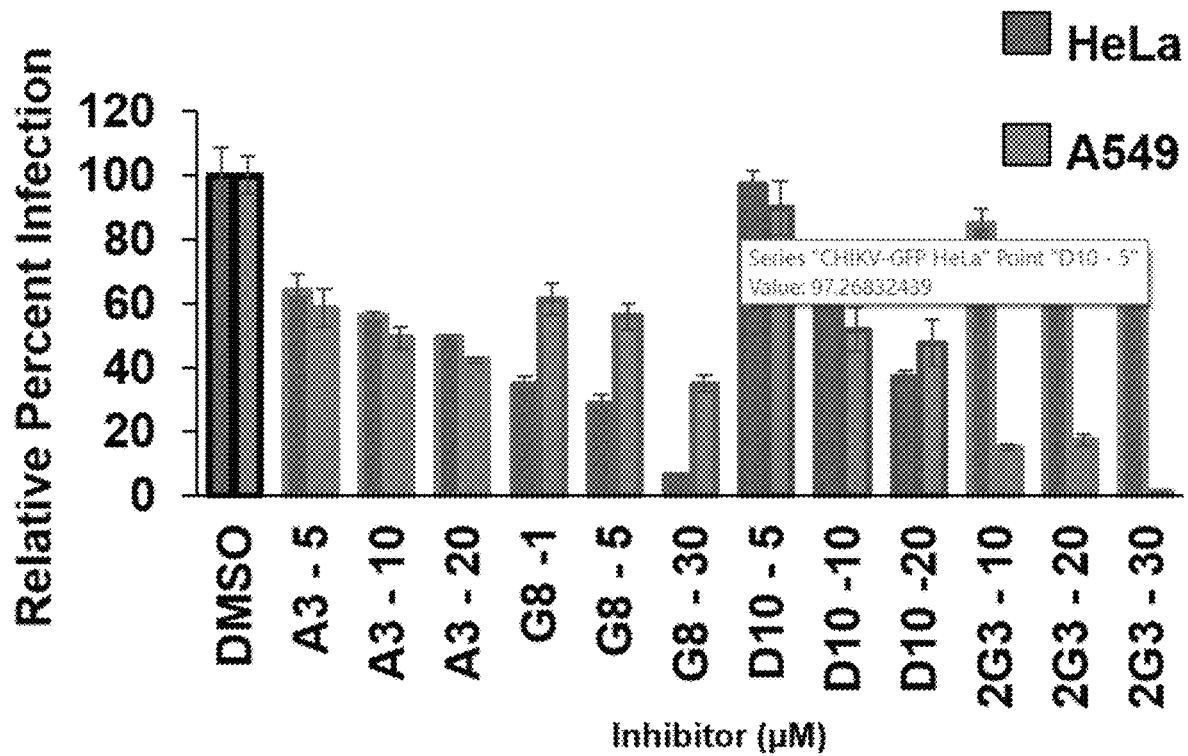
FIG. 9 is a bar graph showing relative percent infection after treatment with the four compounds of interest in HeLa and A549 cells infected with CHIKV-GFP.

In FIG. 9, HeLa (light bars) or A549 cells (dark bars) were treated with indicated concentrations of inhibitors for 1 hour prior to infection, during 3 hour incubation with CHIKV-GFP reporter virus (MOI of 1), and during overnight incubation. The relative percent infection was determined by taking DMSO-treated and infected samples as 100%. Three independent experiments were performed in triplicate. Data are presented as means±SD. It can be seen that in both cell types, all four compounds significantly decreased CHIKV-GFP fluorescence in a concentration dependent manner while maintaining cell viability. While compound III and II, have similar effects on CHIKV-GFP infection in HeLa cells and A549 cells, treatment with compound IV resulted in greater inhibition of virus infection in HeLa cells, whereas compound I treatment was more effective in A549 cells.

Example 12: Characterization of Four Anti-CHIKV Compounds

Figure 10:
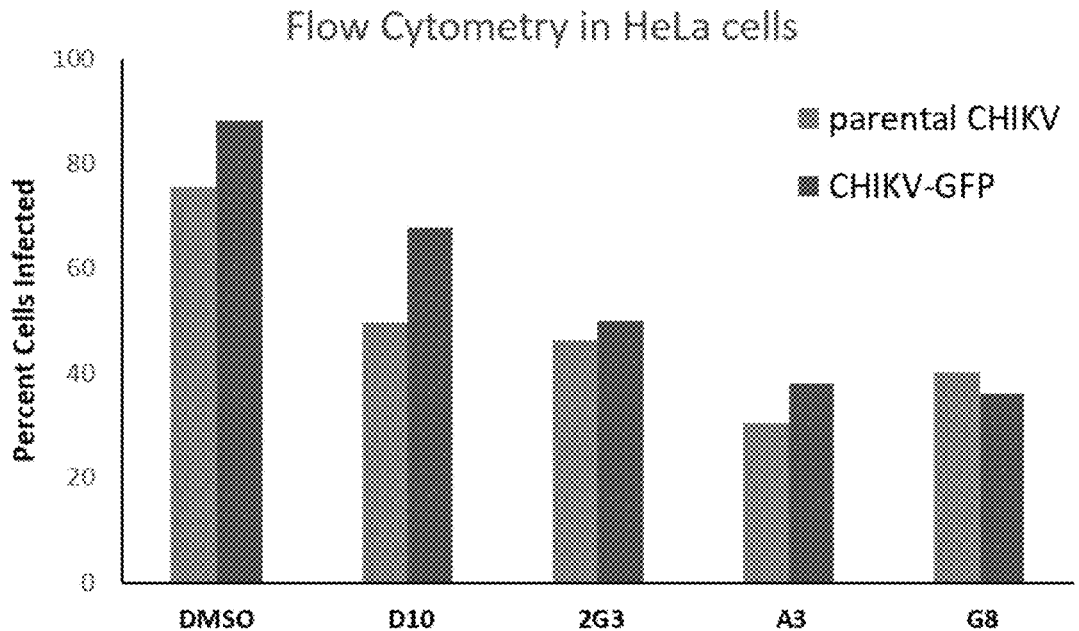
FIG. 10 is bar graph showing flow cytometry data of the compounds in HeLa cells infected with CHIKV (parental) and CHIKV-GFP.

In prior experiments, CHIKV-GFP was measured as total fluorescence per 96-wells, which cannot distinguish differences between the percentage of infected cells, versus the relative viral load per cell, both of which can potentially be reduced due to compound treatment. To validate the results obtained with the plate reader and CHIKV-GFP, flow cytometry and immunostaining were used to quantitatively analyze the percentage of cells infected with CHIKV. HeLa cells were treated with indicated inhibitors for 1 hour prior to and during infection with CHIKV 181/25 and CHIKV-GFP. To measure infection with parental CHIKV 181/25, uninfected and CHIKV 181/25 infected cells were fixed and stained with mouse monoclonal anti-CHIKV antibody. The HeLa cells were treated with 20 μM DMSO, 20 μM D10, 20 μM 2G3, 20 μM A3, or 10 μM G8 for 1 h prior to and during infection with MOI=3 of parental CHIKV (light bars) or CHIKV-GFP (dark bars). The percent cells infected was measured by flow cytometry using mouse anti-CHIKV monoclonal antibody (blue bars) or GFP expression (green bars). The data shown are representative results from three similar experiments. As shown in FIG. 10, CHIKV 181/25 infected cells were compared to uninfected cells probed with the same primary and secondary antibodies. The percentage of cells infected with CHIKV 181/25 and CHIKV-GFP in the presence of these inhibitors was reduced to similar levels as measured by flow cytometry.

Example 13: Assessing Anti-Viral Specificity of the Four Compounds

As mentioned above, the crystal structure of nsP2pro is available for the old world alphaviruses, CHIKV and for the new world alphavirus VEEV and superposition of the two indicates that these proteases have a highly conserved tertiary structure despite only having an amino acid sequence identity of 42% (CHIKV-VEEV). (See Russo, A. T., White, M. A. & Watowich, S. J. The crystal structure of the Venezuelan equine encephalitis alphavirus nsP2 protease. Structure 14, 1449-1458, doi:10.1016/j.str.2006.07.010 (2006); and Saisawang, C. et al. Chikungunya nsP2 protease is not a papain-like cysteine protease and the catalytic dyad cysteine is interchangeable with a proximal serine. Sci Rep 5, 17125, doi:10.1038/srep17125 (2015).)

Figure 11:
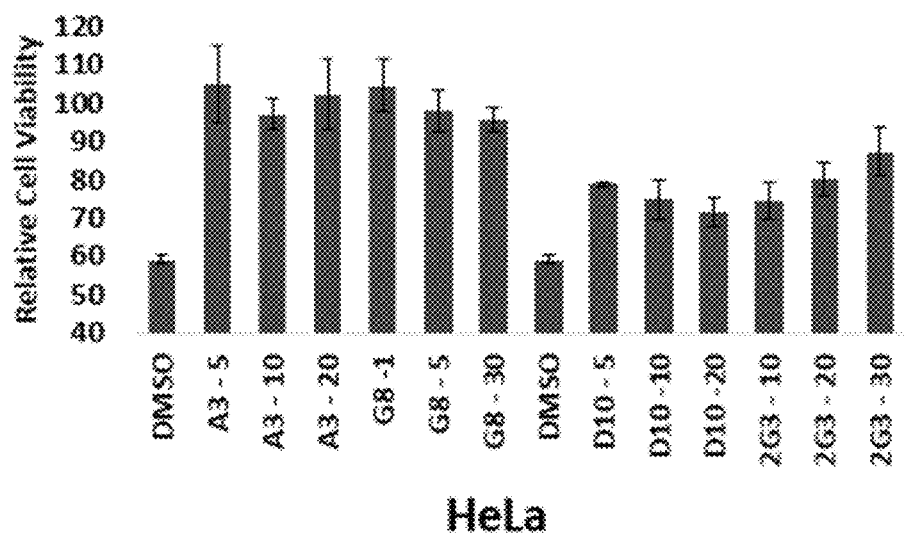
FIG. 11 is a series of bar graphs showing relative percent infection of the four compounds of interest in HeLa and A549 cells of related alphavirus of the alphavirus Venezuelan Equine Encephalitis Virus.
Figure 11:
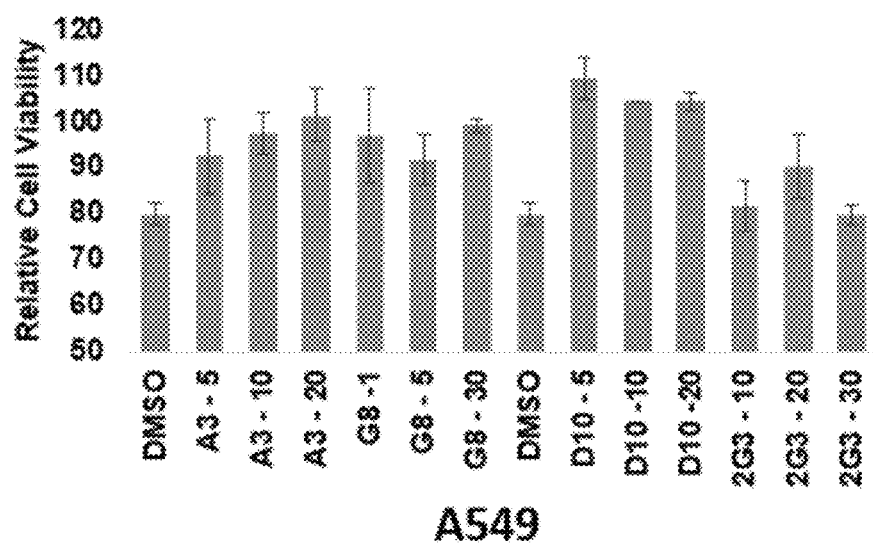

In order to determine if the compounds identified are specific to CHIKV or if they have a broader spectrum of activity, HeLa or A549 cells were treated with indicated doses of inhibitors and measured efficacy against VEEV-induced cytopathic effects using the cell viability indicator PrestoBlue. The results are shown in FIG. 11.

Infection of HeLa cells with VEEV TC-83 for 48 hours reduced cell viability by 40.7% compared to DMSO treated uninfected cells. PrestoBlue fluorescence for VEEV infected cells treated with each compound was normalized to the fluorescence of compound treated uninfected cells to account for background fluorescence or cytopathic effects independent of virus infection. All four compounds reduced VEEV-induced cell death in both cell types in a concentration dependent manner. It should be noted that at 48 hours, 30 μM of compound IV reduced HeLa cell viability by 23.8% and A549 cell viability by 29% (See FIG. 12).

Figure 13:
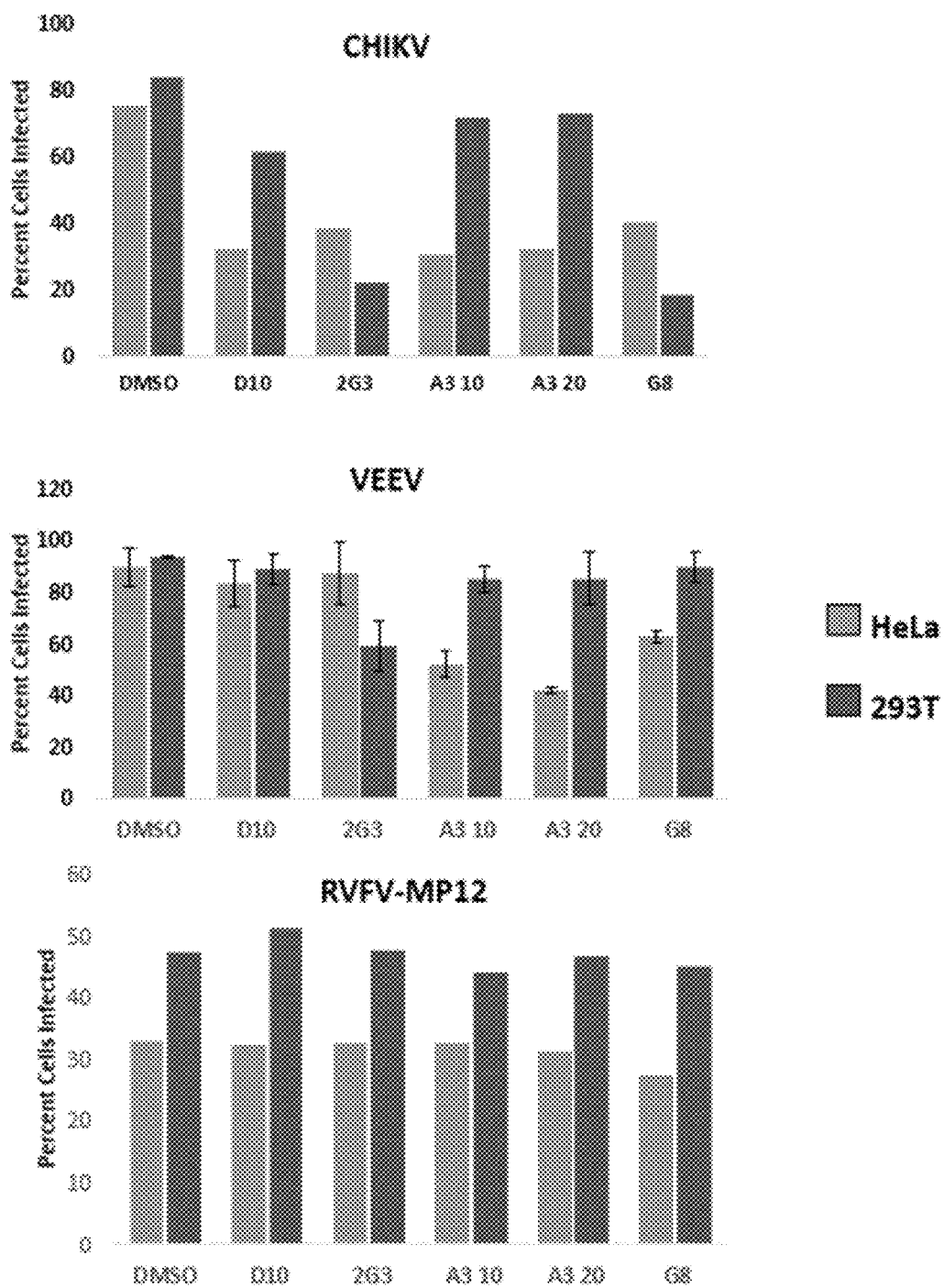
FIG. 13 is a series of bar graphs showing relative percent infection of the four compounds of interest in HeLa and 293T cells of CHIKV 181/25, VEEV, and Rift Valley fever virus (RVFV) strain MP12 at 48 hours.

As shown in FIG. 13, to determine the effect of inhibitors on the percentage of cells infected, flow cytometry and immunostaining was used to quantitatively analyze the percentage of cells infected with CHIKV 181/25, VEEV, and Rift Valley fever virus (RVFV) strain MP12. RVFV was included to characterize the spectrum of inhibition of these compounds. RVFV is a member of the Bunyaviradae family with a negative strand RNA segmented genome that does not encode a protease. Using both HeLa and permissive HEK293T cells, flow cytometry was used to assess the percent infection of the four compounds against parental CHIKV 181/25, VEEV TC-83, and RVFV MP12. A reduction in the percentage of CHIKV 181/25 infected cells was observed in HeLa cells by all four compounds, whereas only compounds III and IV reduced the percentage of VEEV TC-83 infected cells. RVFV MP12 infection was not affected in either cell type. Interestingly, compound III didn't reduce infection of CHIKV 181/25 in HEK293T cells, while compound I was the only compound reducing VEEV TC-83 infection in HEK293T cells. Flow cytometry was done using antibodies against viral capsid proteins, which are produced from a non nsP2-mediated series of cleavage and processing events.

Figure 14:
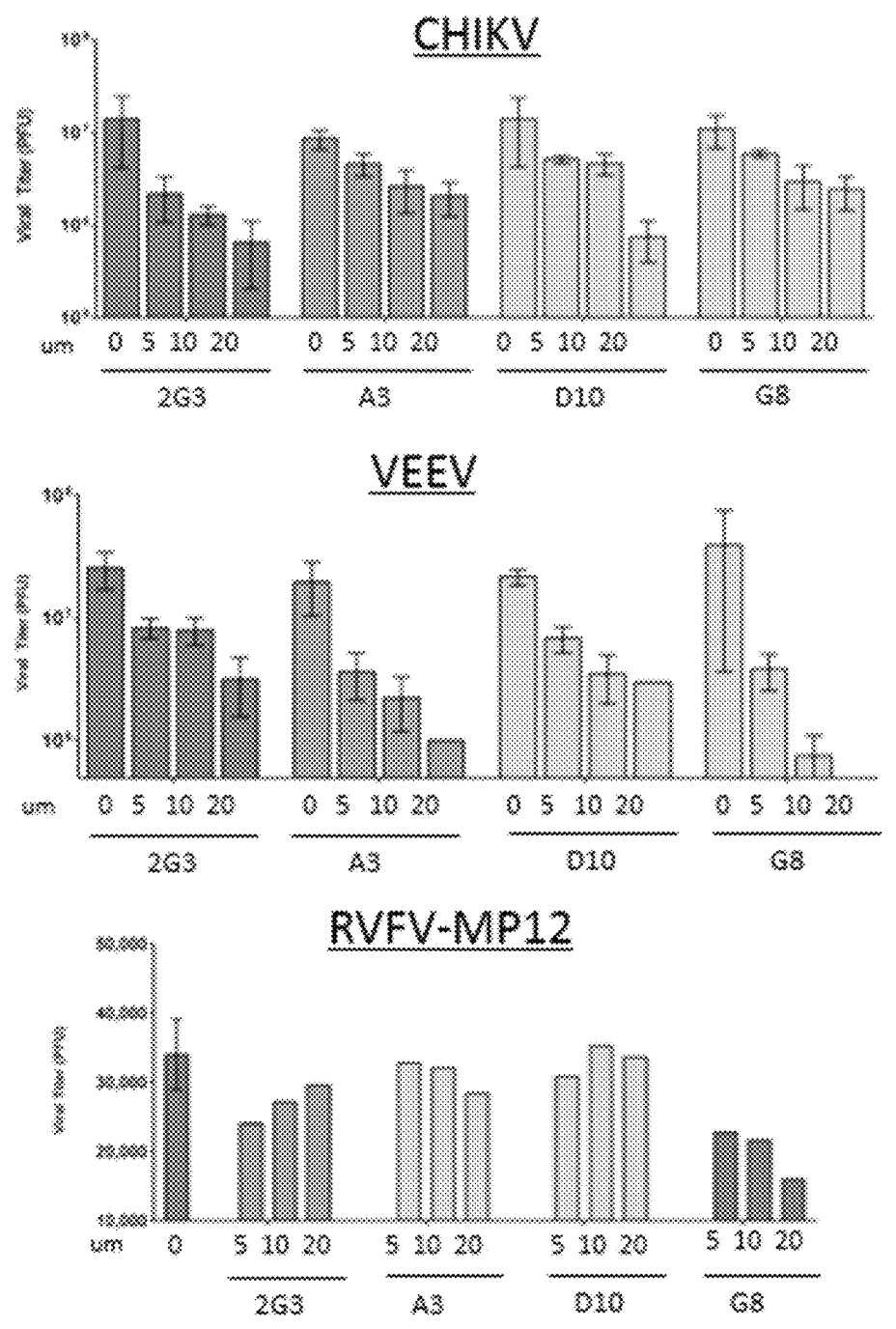

FIG. 14 shows the effect of these four inhibitor compounds on viral growth. Viral titers of parental CHIKV 181/25, VEEV TC-83, and RVFV MP12 were measured in the presence of the inhibitors. HeLa cells were incubated with the compounds at the indicated concentration, and infected with virus. Supernatant was collected and assessed for viral titers at 24 hours post-infection. All four compounds (I-IV) significantly reduced viral titers of CHIKV 181/25, as well as VEEV TC-83, indicating pan-alphavirus specificity. Only one compound, IV, significantly reduced titer of the bunyavirus RVFV with minimal effectiveness seen in compound I. Therefore, compounds were additionally tested against a member of the flavivirus family, Zika virus (ZIKV), for titer reduction (See FIG. 15). Compounds II and I had no obvious reduction in ZIKV viral titer, though compound III showed some minimal effect. Compound IV showed strong reduction of ZIKV viral titer.

Although viral titers in CHIKV 181/25 and VEEV were reduced significantly by all four drugs, a determination of whether delaying application of the compounds later into the viral replication cycle would still exert comparable anti-viral effects was sought after. Accordingly, an assay was performed by adding compound treatment prior to, concurrent with, or at various timepoints post CHIKV 181/25-inoculation. At all timepoints, viral titer was significantly reduced. Compounds I, II, and III showed relatively similar reduction of viral titer across all timepoints, whereas compound IV showed the strongest reduction with pre-treatment, with lessened efficacy at each consecutive timepoint.

CONCLUSIONS

Using the Chikungunya virus nsP2pro, 40,000 compounds were screened and dozens of candidate anti-viral compounds were identified that show some efficacy in cell culture. Four of these compounds were characterized in a variety of assays, showing reduction in viral protein levels, reduced cellular effects, and a pronounced reduction of viral titers. These compounds additionally work against the closely related Venezuelan Equine Encephalitis Virus, another alphavirus that is a biomedical threat and priority pathogen.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim. The term "consisting essentially" as used herein means the specified materials or steps and those that do not materially affect the basic and novel characteristics of the material or method. Unless the context indicates otherwise, all percentages and averages are by weight. If not specified above, the properties mentioned herein may be determined by applicable ASTM standards, or if an ASTM standard does not exist for the property, the most commonly used standard known by those of skill in the art may be used.

It is claimed:
1. A pharmaceutical composition comprising:
a compound selected from the group consisting of compounds I-IV

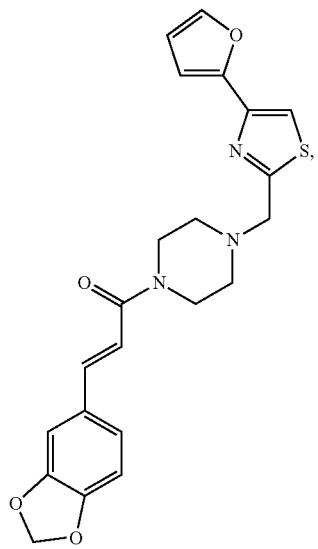

I

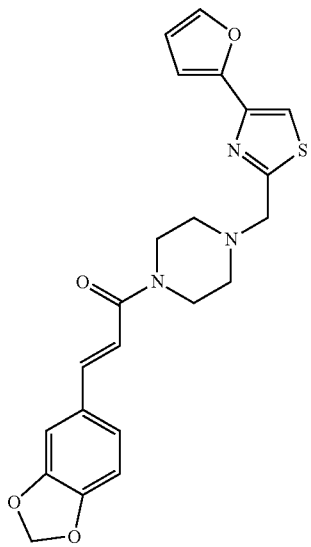

I.

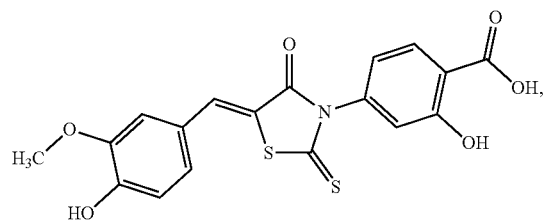

II

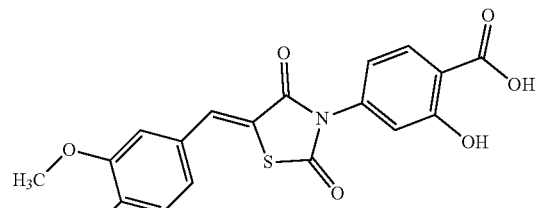

II.

6. The composition of claim 1, comprising the compound of formula II

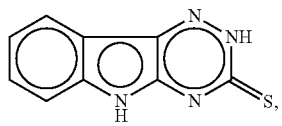

III

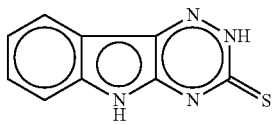

III.

7. The composition of claim 1, comprising the compound of formula III

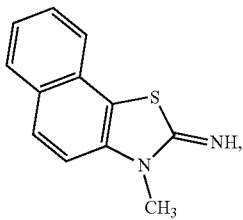

IV

8. The composition of claim 1, comprising the compound of formula IV

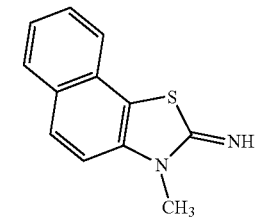

IV.

pharmaceutically acceptable salts thereof, or combinations of any of these; and
a pharmaceutically acceptable excipient;
wherein if compound III, a pharmaceutically acceptable salt thereof, or a combination of any of these is selected, the composition is formulated for oral or parenteral delivery.
2. The composition of claim 1, wherein the composition is formulated for oral delivery.
3. The composition of claim 1, wherein the composition is formulated for parenteral delivery.
4. The composition of claim 1, wherein the compound is present in the pharmaceutical composition in an amount of 1 mg to 2 g of the pharmaceutical composition.
5. The composition of claim 1, comprising the compound of formula I 9. The composition of claim 1, wherein the compound is the pharmaceutically acceptable salt of the compound selected from compounds I-IV.
10. The composition of claim 1, wherein the compound has a IC50 of less than 50 μM against an alphavirus.

11. A method of treatment for an alphavirus or Rift Valley Fever infection, comprising:
administering to a patient in need thereof a therapeutically effective amount of a pharmaceutical composition comprising a compound selected from the group consisting of compounds I-IV

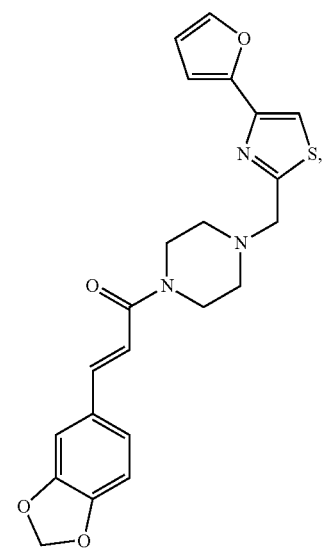

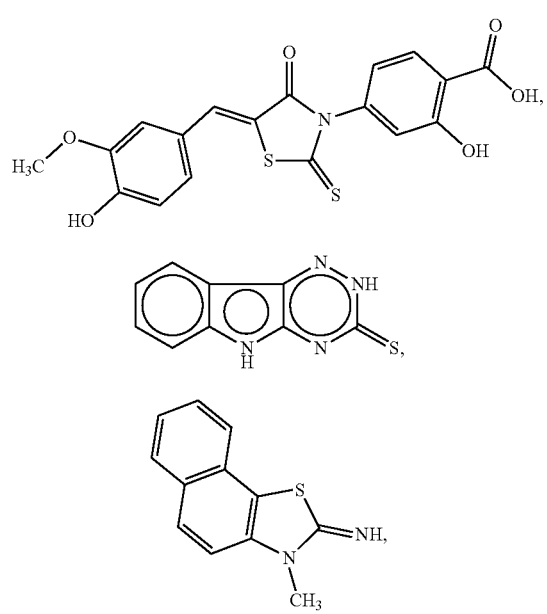

pharmaceutically acceptable salts thereof, or combinations of any of these; and
a pharmaceutically acceptable excipient.

12. The method of claim 11, wherein the alphavirus is Chikungunya virus, Venezuelan Equine Encephalitis virus, Sindbis virus, O'nyong-nyong virus, Ross River virus, Barmah Forest virus, Semiliki Forest virus, Eastern equine encephalitis virus (EEEV), or Western equine encephalitis virus (WEEV).

13. The method of claim 11, wherein the infection is a Chikungunya virus infection, Venezuelan Equine Encephalitis virus infection, or Rift Valley Fever Virus infection.

14. The method of claim 11, wherein the compound is present in the pharmaceutical composition in an amount of 1 mg to 2 g of the pharmaceutical composition.

15. The method of claim 11, wherein the compound includes the compound of formula I

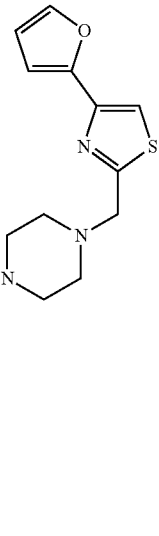

16. The method of claim 11, wherein the compound includes the compound of formula II 17. The method of claim 11, wherein the compound includes the compound of formula III 18. The method of claim 11, wherein the compound includes the compound of formula IV 19. The method of claim 11, wherein the compound is the pharmaceutically acceptable salt of the compound selected from compounds I-IV.

20. A method of treatment for an Zika virus infection, comprising:
administering to a patient in need thereof a therapeutically effective amount of a compound selected from the group consisting of compound IV
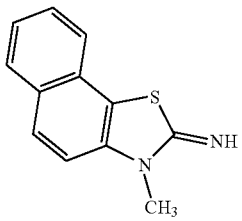
IV.
pharmaceutically acceptable salts thereof, or combinations of any of these; and
a pharmaceutically acceptable excipient.
* * * * *

SEQUENCE LISTING

```
<160> NUMBER OF SEQ ID NOS: 3

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Glu Ala Gly Cys
1

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 2

His His His His His His
1               5

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
caaggtttcc gattatggt                                                      19
```